US010323077B2

(12) United States Patent
Spencer et al.

(10) Patent No.: US 10,323,077 B2
(45) Date of Patent: Jun. 18, 2019

(54) EXPRESSION OF CHIMERIC POLYPEPTIDE WITH VARIABLE LYMPHOCYTE RECEPTORS ON IMMUNE CELLS AND USES FOR TREATING CANCER

(71) Applicants: Emory University, Atlanta, GA (US); Children's Healthcare of Atlanta, Inc., Atlanta, GA (US)

(72) Inventors: H. Trent Spencer, Marietta, GA (US); Christopher B. Doering, Atlanta, GA (US); Brantley R. Herrin, Decatur, GA (US); Max Dale Cooper, Atlanta, GA (US)

(73) Assignees: Emory University, Atlanta, GA (US); Children's Healthcare of Atlanta, Atlanta, GA (US)

( * ) Notice: Subject to any disclaimer, the term of this patent is extended or adjusted under 35 U.S.C. 154(b) by 0 days.

(21) Appl. No.: 15/117,811

(22) PCT Filed: Feb. 9, 2015

(86) PCT No.: PCT/US2015/014975
§ 371 (c)(1),
(2) Date: Aug. 10, 2016

(87) PCT Pub. No.: WO2015/120363
PCT Pub. Date: Aug. 13, 2015

(65) Prior Publication Data
US 2017/0008947 A1 Jan. 12, 2017

Related U.S. Application Data

(60) Provisional application No. 61/938,057, filed on Feb. 10, 2014.

(51) Int. Cl.
*C07K 14/705* (2006.01)
*A61K 39/00* (2006.01)
*C07K 14/725* (2006.01)
*C07K 14/46* (2006.01)
*A61K 35/17* (2015.01)
*A61K 45/06* (2006.01)
*C12N 15/85* (2006.01)
*A61K 38/00* (2006.01)
*A61K 35/12* (2015.01)

(52) U.S. Cl.
CPC ........ *C07K 14/70521* (2013.01); *A61K 35/17* (2013.01); *A61K 45/06* (2013.01); *C07K 14/461* (2013.01); *C07K 14/7051* (2013.01); *C07K 14/70503* (2013.01); *C12N 15/85* (2013.01); *A61K 38/00* (2013.01); *A61K 2035/124* (2013.01); *C07K 2319/02* (2013.01); *C07K 2319/03* (2013.01); *C07K 2319/33* (2013.01); *C07K 2319/70* (2013.01)

(58) Field of Classification Search
None
See application file for complete search history.

(56) References Cited

U.S. PATENT DOCUMENTS

| 8,039,588 | B2 | 10/2011 | Pancer | |
|---|---|---|---|---|
| 8,212,018 | B2 | 7/2012 | Pancer | |
| 2011/0165584 | A1 | 7/2011 | Pancer | |
| 2011/0230374 | A1 | 9/2011 | Pancer | |
| 2012/0189640 | A1 | 7/2012 | Cooper | |
| 2013/0287748 | A1* | 10/2013 | June | A61K 35/17 424/93.21 |
| 2014/0271635 | A1 | 9/2014 | Brogdon | |
| 2015/0266973 | A1* | 9/2015 | Jarjour | C07K 14/7056 424/93.21 |

FOREIGN PATENT DOCUMENTS

| WO | 2008016854 | 2/2008 |
|---|---|---|
| WO | 2010065407 | 6/2010 |
| WO | 2011053750 | 5/2011 |
| WO | 2012079000 | 6/2012 |
| WO | 2013040371 | 3/2013 |
| WO | 2013078425 | 5/2013 |
| WO | 2013154760 | 10/2013 |

OTHER PUBLICATIONS

Herrin et al., Structure and specificity of lamprey monoclonal antibodies. PNAS, 2008, 105:2040-2045 (Year: 2008).*
Zhang et al., Alteration in the IL-2 signal peptide affects secretion of proteins in vitro and in vivo. J Gene Med 2005; 7: 354-365. (Year: 2005).*
Kim et al, Crystal Structure of the TLR4-MD-2 Complex with Bound Endotoxin Antagonist Eritoran. Cell 130, 906-917, Sep. 7, 2007 (Year: 2007).*
Sawai et al., Protection and in Vivo Selection of Hematopoietic Stem Cells Using Temozolomide, O6-Benzylguanine, and an Alkyltransferase-Expressing Retroviral Vector. Molecular Therapy vol. 3, No. 1, Jan. 2001, pp. 78-87 (Year: 2001).*

(Continued)

*Primary Examiner* — Kevin K Hill
*Assistant Examiner* — Arthur S Leonard
(74) *Attorney, Agent, or Firm* — Emory Patent Group

(57) ABSTRACT

This disclosure relates to recombinant cellular expression of chimeric proteins with peptide sequences derived from lymphocyte receptors and uses for treating cancer. In certain embodiments, the disclosure relates to a recombinant vector comprising a nucleic acid that encodes a chimeric protein with a segment with a targeting moiety based on a variable lymphocyte receptor (VLR) capable of binding a tumor associated antigen and a segment with a T cell signal transduction subunit. In certain embodiments, the recombinant vectors are used in immune based cancer treatments.

11 Claims, 6 Drawing Sheets
Specification includes a Sequence Listing.

(56) References Cited

OTHER PUBLICATIONS

Klitgaard et al., Combination of two anti-CD5 monoclonal antibodies synergistically induces complement-dependent cytotoxicity of chronic lymphocytic leukaemia cells. British Journal of Haematology, 2013, 163, 182-193. (Year: 2013).*
Brentjens et al. CD19-targeted T cells rapidly induce molecular remissions in adults with chemotherapy-refractory acute lymphoblastic leukemia, Sci Transl Med. 2013, 5(177): 177ra38.
Dasgupta et al. Engineered drug resistant immunocompetent cells enhance tumor cell killing during a chemotherapy challenge, Biochem Biophys Res Commun. 2010, 391(1): 170-175.
Grupp et al. Chimeric Antigen Receptor—Modified T Cells for Acute Lymphoid Leukemia, N Engl J Med 2013, 368:1509-18.
Guo et al. Dual Nature of the Adaptive Immune System in Lampreys, Nature. 2009, 459(7248): 796-801.
Han et al. Antigen Recognition by Variable Lymphocyte Receptors, Science. 2008, 321(5897): 1834-1837.
Hirano et al. The Evolution of Adaptive Immunity in Vertebrates, Advances in Immunology, vol. 109, 125-157.
Maude et al. Chimeric Antigen Receptor T Cells for Sustained Remissions in Leukemia, N Engl J Med 2014, 371:1507-17.
Nakahara et al. Chronic lymphocytic leukemia monitoring with a lamprey idiotope-specific antibody, Cancer Immunol Res. 2013, 1(4): 223-228.
Porter et al. Chimeric Antigen Receptor—Modified T Cells in Chronic Lymphoid Leukemia, N Engl J Med 2011, 365:725-33.
Tasumi et al High-affinity lamprey VLRA and VLRB monoclonal antibodies, PNAS , 2009, vol. 106, No. 31, 12891-12896.
Yu et al. Purification and identification of cell surface antigens using lamprey monoclonal antibodies, Immunol Methods. 2012, 386(0): 43-49.
Yu et al. A lamprey monoclonal VLR antibody recognizes a novel plasma cell antigen, J Immunol May 1, 2013, 190 (1 Supplement) 114.11.
Yu et al. Identification of human plasma cells with a lamprey monoclonal antibody, JCI Insight. 2016, 1(3):e84738.
Alder et al. Diversity and Function of Adaptive Immune Receptors in a Jawless Vertebrate, Science, 310, 1970 (2005).
Collins et al. Crystal structure of an anti-idiotype variable lymphocyte receptor, Acta Cryst. (2017). F73, 682-687.
Collins et al. Structural Insights into VLR Fine Specificity for Blood Group Carbohydrates, 2017, Structure, 25, 1667-1678.
Gunn et al. VLR Recognition of TLR5 Expands the Molecular Characterization of Protein Antigen Binding by Non-Ig-based Antibodies, J Mol Biol (2018) 430, 1350-1367.
European Search Report for EP application No. 15746077.5 dated Jun. 29, 2017.
European communication for EP application No. 15746077.5 dated Jul. 24, 2018.

* cited by examiner

GCATGTCCCTCGCAGTGTTCGTGCTCAGGGACACAAGTGAACTGCCATGAGAGAAGCC
TCGCGTCTGTGCCTGCGGGAATCCCCACCACCACGCAAGTGCTGTATTTGTACACCAAT
CAGATCACGAAGCTCGAGCCCGGCGTGTTTGACAGTCTGACGCAACTGACTGAACTGT
ACCTTAGTGCCAACCAGCTCACGACTCTACCCGAGGGGGTGTTTGACAAACTGACCAA
ACTCACTCATCTGAGTCTGTACAATAACCAGCTGAAGAGCATTCCTAGGGGCGCCTTTG
ACAACCTCAAGAGCCTCACTCACATCTGGCTGTCCAGCAACCCCTGGGACTGTCAGTGC
ACGGACATCCTCTACTTGAGTGGCTGGGTCGCTCAGCACTCGGGCATCGTGGGTGAGGG
GTGGCCATGGAGGCACAGTCCAGACAGCGTCAAGTGCTCTGGTACCAATACCCCCGTC
CGTGCGGTCACCGAGGCCAGCACTAGCCCCTCGAAATGCCCAGGCTACGTTGCTACGA
CCACG (SEQ ID NO: 3)

FIG. 1A

ACPSQCSCSGTQVNCHERSLASVPAGIPTTTQVLYLYTNQITKLEPGVFDSLTQLTELYLSAN
QLTTLPEGVFDKLTKLTHLSLYNNQLKSIPRGAFDNLKSLTHIWLSSNPWDCQCTDILYLSG
WVAQHSGIVGEGWPWRHSPDSVKCSGTNTPVRAVTEASTSPSKCP (SEQ ID NO: 4)

FIG. 1B

GCATGTCCCTCGCAGTGTTCGTGCTCAGGGACAACTGTGGATTGTAGTGGGAAAAGCCT
CGCATCTGTGCCTGCAGGAATCCCCATCACCACGCAGTCTCTGTATTTGCTCGTCAATC
AAATCACGAAGCTCGAGCCTGGGGTGTTTGACCATCTGGTGAATCTGCAGAAGCTCTAT
TTGAGTGGGAATCAGCTGCAGGCTCTACCCGTTGGGGTGTTTGACAAACTGACCCAGCT
CACTTATCTGGGTCTGGACGCCAACCAACTGAAGAGCATCGTCAGGGGCGCCTTTGACA
ACCTCAAGAGCCTCACTCACATCTGGCTGTACAACAACCCCTGGGACTGTGCCTGCTCA
GACATCCTGTACCTCAGTCGCTGGATCTCTCAGCACCCAGGAGTCTTGAGGAATCCTGG
TTCCTACAATGTCAACCCCGACTCAGCACTCTGCTCTGGTACCAATACCCCCGTCCGTG
CGGTCACCGAGGCCAGCACTAGCCCCTCGAAATGCCCAGGCTACGTTGCTACGACCAC
G (SEQ ID NO: 5)

FIG. 1C

ACPSQCSCSGTTVDCSGKSLASVPAGIPITTQSLYLLVNQITKLEPGVFDHLVNLQKLYLSGN
QLQALPVGVFDKLTQLTYLGLDANQLKSIVRGAFDNLKSLTHIWLYNNPWDCACSDILYLS
RWISQHPGVLRNPGSYNVNPDSALCSGTNTPVRAVTEASTSPSKCP (SEQ ID NO: 6)

FIG. 1D

GCATGTCCCTCGCAGTGTTCGTGCGATCAGACAACTGTATACTGCCATAGCAGACGCCT
CACGTCTGTGCCTGCAGGAATCCCCACCACAACGCGAGTGCTGTATTTGAACAGCAATC
AGATCACGAAGCTCGAGCCCGGGGTGTTTGACCGCCTGGTGAATCTGCAGAAGCTCTAT
TTGAGTGGGAATCAGCTGCAGGCTCTTCCTGAGGGGGTGTTTGACCGCCTGGTGAATCT
GCAGAAGCTGTGGTTGAACAGCAACCAGCTGACCTCTCTCCCCGCTGGTGTGTTTGACC
GTCTGACTCAACTGACACGACTGGATCTTGGTGGCAACCAGCTGAAGGCCCTTCGCGAA
GGGATGTTTGACCGCTTGGTTAATCTGCAGACGCTGGATTTGCACAACAACCAGCTGAA
GAGCATTCCTAGGGGCGCCTTTGACAACCTCAAGAGCCTCACTAACATCTATCTGTACA
GTAACCCCTGGGACTGCGAGTGTTCGGACATCCTCTATCTGAAGAACTGGATTGTGCAG
CATGCAAGCATCGTGAATCTACGGGGCCATGGGGAGTTGATAACGTGAAGTGCTCTG
GTACCAATACCCCCGTCCGTGCGGTCACCGAGGCCAGCACTAGCCCCTCGAAATGCCCA
GGCTACGTTGCTACGACCACG (SEQ ID NO: 7)

FIG. 1E

ACPSQCSCDQTTVYCHSRRLTSVPAGIPTTTRVLYLNSNQITKLEPGVFDRLVNLQKLYLSG
NQLQALPEGVFDRLVNLQKLWLNSNQLTSLPAGVFDRLTQLTRLDLGGNQLKALREGMFD
RLVNLQTLDLHNNQLKSIPRGAFDNLKSLTNIYLYSNPWDCECSDILYLKNWIVQHASIVNL
RGHGGVDNVKCSGTNTPVRAVTEASTSPSKCP (SEQ ID NO: 8)

FIG. 1F

TGTCCTTCACAGTGCTCCTGCAGCGGAACCGAGGTCCATTGTCAGAGAAAATCCCTGGC
TTCAGTCCCTGCCGGAATCCCAACCACAACAAGGGTGCTGTACCTGCACGTCAACGAG
ATTACTAAGTTCGAACCAGGAGTGTTTGACCGCCTGGTCAACCTGCAGCAGCTGTATCT
GGGAGGAAATCAGCTGAGCGCCCTGCCAGACGGCGTGTTCGATCGACTGACTCAGCTG
ACCAGACTGGATCTGTACAACAATCAGCTGACCGTGCTGCCTGCCGGGGTCTTTGACCG
ACTGGTGAATCTGCAGACACTGGATCTGCACAACAATCAGCTGAAGTCTATCCCCAGA
GGCGCATTCGACAACCTGAAAAGTCTGACCCATATTTGGCTGTTTGGGAATCCTTGGGA
CTGCGCCTGTAGCGATATCCTGTATCTGTCCGGATGGCTGGGACAGCATGCAGGGAAA
GAGCAGGGACAGGCTGTCTGCTCTGGCACCAACACACCCGTGCGGGCTGTCACCGAGG
CATCAACATCCCCATCAAAGTGTCCTGGCTACGTGGCAACAACCAGATCTGCTAGCGAG
CAGAAG (SEQ ID NO: 9)

FIG. 2A

CPSQCSCSGTEVHCQRKSLASVPAGIPTTTRVLYLHVNEITKFEPGVFDRLVNLQQLYLGGN
QLSALPDGVFDRLTQLTRLDLYNNQLTVLPAGVFDRLVNLQTLDLHNNQLKSIPRGAFDNL
KSLTHIWLFGNPWDCACSDILYLSGWLGQHAGKEQGQAVCSGTNTPVRAVTEASTSPSKCP
(SEQ ID NO: 10)
FIG. 2B
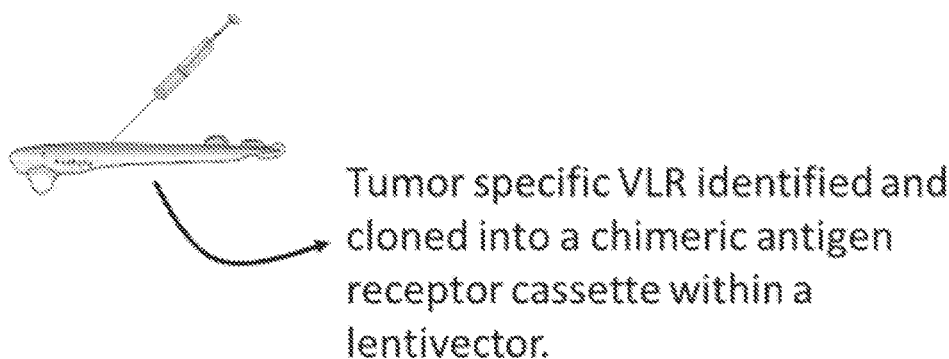
FIG. 3
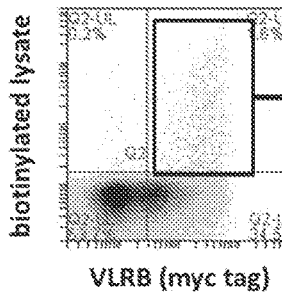
FIG. 4A
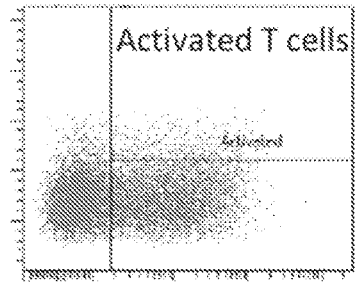
FIG. 4B

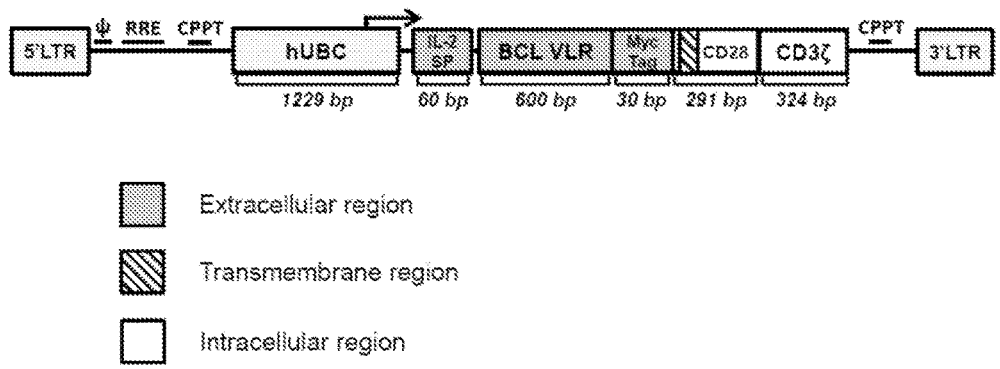
FIG. 5
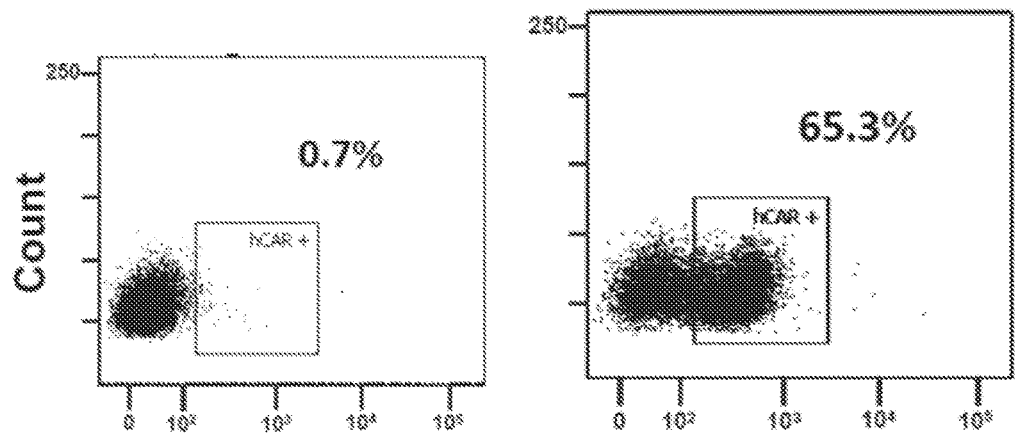
FIG. 6A
FIG. 6B
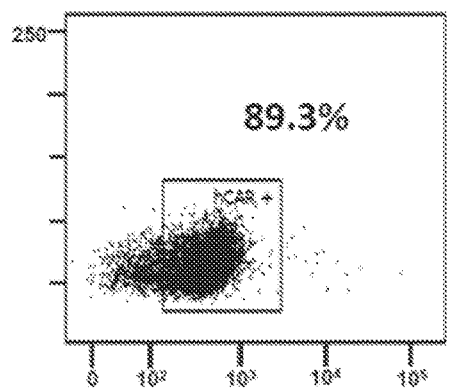
FIG. 6C

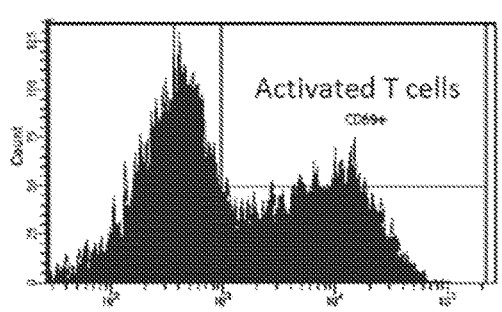
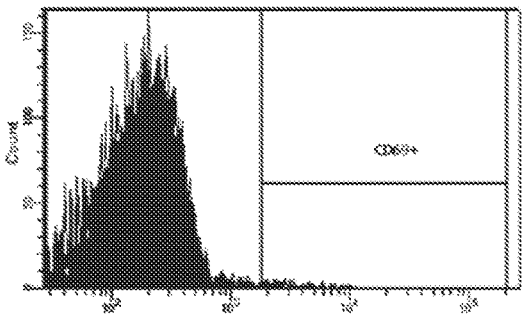
FIG. 8A          FIG. 8B
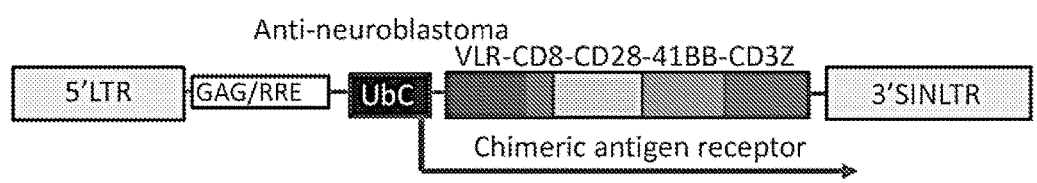
FIG. 9A
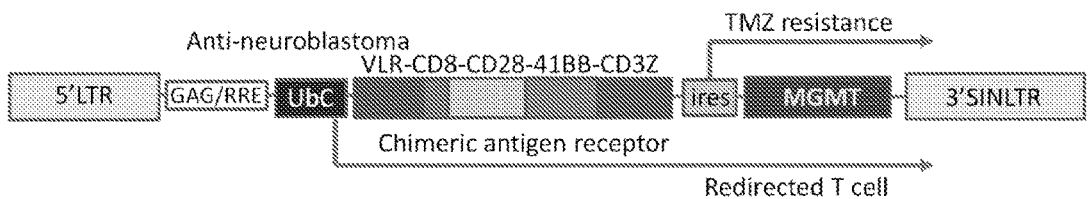
FIG. 9B

SEQUENCE LISTING

<160> NUMBER OF SEQ ID NOS: 23

<210> SEQ ID NO 1
<211> LENGTH: 7
<212> TYPE: PRT
<213> ORGANISM: Artificial Sequence

```
<220> FEATURE:
<223> OTHER INFORMATION: Synthetic construct
<220> FEATURE:
<221> NAME/KEY: MISC_FEATURE
<222> LOCATION: (1)..(2)
<223> OTHER INFORMATION: Where X is any amino acid
<220> FEATURE:
<221> NAME/KEY: MISC_FEATURE
<222> LOCATION: (4)..(4)
<223> OTHER INFORMATION: Where X is any amino acid
<220> FEATURE:
<221> NAME/KEY: MISC_FEATURE
<222> LOCATION: (6)..(7)
<223> OTHER INFORMATION: Where X is any amino acid

<400> SEQUENCE: 1

Xaa Xaa Leu Xaa Leu Xaa Xaa
1               5

<210> SEQ ID NO 2
<211> LENGTH: 62
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: where X is any amino acid
<220> FEATURE:
<221> NAME/KEY: MISC_FEATURE
<222> LOCATION: (4)..(7)
<223> OTHER INFORMATION: where X is any amino acid
<220> FEATURE:
<221> NAME/KEY: MISC_FEATURE
<222> LOCATION: (9)..(9)
<223> OTHER INFORMATION: where X is any amino acid
<220> FEATURE:
<221> NAME/KEY: MISC_FEATURE
<222> LOCATION: (14)..(14)
<223> OTHER INFORMATION: where X is any amino acid
<220> FEATURE:
<221> NAME/KEY: MISC_FEATURE
<222> LOCATION: (20)..(21)
<223> OTHER INFORMATION: where X is any amino acid
<220> FEATURE:
<221> NAME/KEY: MISC_FEATURE
<222> LOCATION: (23)..(26)
<223> OTHER INFORMATION: where X is any amino acid
<220> FEATURE:
<221> NAME/KEY: MISC_FEATURE
<222> LOCATION: (28)..(28)
<223> OTHER INFORMATION: where X is any amino acid
<220> FEATURE:
<221> NAME/KEY: MISC_FEATURE
<222> LOCATION: (32)..(33)
<223> OTHER INFORMATION: where X is any amino acid
<220> FEATURE:
<221> NAME/KEY: MISC_FEATURE
<222> LOCATION: (39)..(39)
<223> OTHER INFORMATION: where X is any amino acid
<220> FEATURE:
<221> NAME/KEY: MISC_FEATURE
<222> LOCATION: (41)..(42)
<223> OTHER INFORMATION: where X is any amino acid
<220> FEATURE:
<221> NAME/KEY: MISC_FEATURE
<222> LOCATION: (44)..(47)
<223> OTHER INFORMATION: where X is any amino acid
<220> FEATURE:
<221> NAME/KEY: MISC_FEATURE
<222> LOCATION: (49)..(50)
<223> OTHER INFORMATION: where X is any amino acid
<220> FEATURE:
<221> NAME/KEY: MISC_FEATURE
<222> LOCATION: (52)..(52)
<223> OTHER INFORMATION: where X is any amino acid
```

```
<220> FEATURE:
<221> NAME/KEY: MISC_FEATURE
<222> LOCATION: (54)..(56)
<223> OTHER INFORMATION: where X is any amino acid
<220> FEATURE:
<221> NAME/KEY: MISC_FEATURE
<222> LOCATION: (58)..(58)
<223> OTHER INFORMATION: where X is any amino acid
<220> FEATURE:
<221> NAME/KEY: MISC_FEATURE
<222> LOCATION: (60)..(60)
<223> OTHER INFORMATION: where X is any amino acid

<400> SEQUENCE: 2

Val Xaa Cys Xaa Xaa Xaa Leu Xaa Ser Val Pro Ala Xaa Ile Pro
 1               5                  10                  15

Thr Thr Thr Xaa Xaa Leu Xaa Xaa Xaa Asn Xaa Ile Thr Lys Xaa
             20                  25                  30

Xaa Pro Gly Val Phe Asp Xaa Leu Xaa Xaa Leu Xaa Xaa Xaa Leu
         35                  40                  45

Xaa Xaa Asn Xaa Leu Xaa Xaa Xaa Pro Xaa Gly Xaa Phe Asp
 50                  55                  60

<210> SEQ ID NO 3
<211> LENGTH: 531
<212> TYPE: PRT
<213> ORGANISM: Artificial Sequence
<220> FEATURE:
<223> OTHER INFORMATION: Synthetic construct

<400> SEQUENCE: 3

Gly Cys Ala Thr Gly Thr Cys Cys Thr Cys Gly Cys Ala Gly Thr
 1               5                  10                  15

Gly Thr Thr Cys Gly Thr Gly Cys Thr Cys Ala Gly Gly Ala Cys
             20                  25                  30

Ala Cys Ala Ala Gly Thr Gly Ala Ala Cys Thr Gly Cys Ala Thr
         35                  40                  45

Gly Ala Gly Ala Gly Ala Ala Gly Cys Cys Thr Cys Gly Cys Gly Thr
 50                  55                  60

Cys Thr Gly Thr Gly Cys Cys Thr Gly Cys Gly Gly Ala Ala Thr
65                  70                  75                  80

Cys Cys Cys Cys Ala Cys Cys Ala Cys Cys Ala Cys Gly Cys Ala Ala
                 85                  90                  95

Gly Thr Gly Cys Thr Gly Thr Ala Thr Thr Thr Gly Thr Ala Cys Ala
             100                 105                 110

Cys Cys Ala Ala Thr Cys Ala Gly Ala Thr Cys Ala Cys Gly Ala Ala
             115                 120                 125

Gly Cys Thr Cys Gly Ala Gly Cys Cys Gly Gly Cys Gly Thr Gly
             130                 135                 140

Thr Thr Thr Gly Ala Cys Ala Gly Thr Thr Gly Ala Cys Gly Cys
145                 150                 155                 160

Ala Ala Cys Thr Gly Ala Cys Thr Gly Ala Cys Thr Gly Thr Ala
                 165                 170                 175

Cys Cys Thr Thr Ala Gly Thr Gly Cys Cys Ala Ala Cys Cys Ala Gly
             180                 185                 190

Cys Thr Cys Ala Cys Gly Ala Cys Thr Cys Thr Ala Cys Cys Gly
             195                 200                 205

Ala Gly Gly Gly Gly Gly Thr Gly Thr Thr Thr Gly Ala Cys Ala Ala
             210                 215                 220
```

```
Ala Cys Thr Gly Ala Cys Cys Ala Ala Ala Cys Thr Cys Ala Cys Thr
225                 230                 235                 240
Cys Ala Thr Cys Thr Gly Ala Gly Thr Cys Thr Gly Thr Ala Cys Ala
                245                 250                 255
Ala Thr Ala Ala Cys Cys Ala Gly Cys Thr Gly Ala Ala Gly Ala Gly
            260                 265                 270
Cys Ala Thr Cys Cys Thr Ala Gly Gly Gly Cys Gly Cys Cys
        275                 280                 285
Thr Thr Thr Gly Ala Cys Ala Cys Cys Thr Cys Ala Ala Gly Ala
    290                 295                 300
Gly Cys Cys Thr Cys Ala Cys Thr Cys Ala Thr Cys Thr Gly
305                 310                 315                 320
Gly Cys Thr Gly Thr Cys Cys Ala Gly Cys Ala Ala Cys Cys Cys
                325                 330                 335
Thr Gly Gly Gly Ala Cys Thr Gly Thr Cys Ala Gly Thr Gly Cys

```
Phe Asp Ser Leu Thr Gln Leu Thr Glu Leu Tyr Leu Ser Ala Asn Gln
 50                  55                  60
Leu Thr Thr Leu Pro Glu Gly Val Phe Asp Lys Leu Thr Lys Leu Thr
 65                  70                  75                  80
His Leu Ser Leu Tyr Asn Asn Gln Leu Lys Ser Ile Pro Arg Gly Ala
                 85                  90                  95
Phe Asp Asn Leu Lys Ser Leu Thr His Ile Trp Leu Ser Ser Asn Pro
            100                 105                 110
Trp Asp Cys Gln Cys Thr Asp Ile Leu Tyr Leu Ser Gly Trp Val Ala
                115                 120                 125
Gln His Ser Gly Ile Val Gly Glu Gly Trp Pro Trp Arg His Ser Pro
130                 135                 140
Asp Ser Val Lys Cys Ser Gly Thr Asn Thr Pro Val Arg Ala Val Thr
145                 150                 155                 160
Glu Ala Ser Thr Ser Pro Ser Lys Cys Pro
                165                 170
```

<210> SEQ ID NO 5
<211> LENGTH: 531
<212> TYPE: PRT
<213> ORGANISM: Artificial Sequence
<220> FEATURE:
<223> OTHER INFORMATION: Synthetic construct

<400> SEQUENCE: 5

```
Gly Cys Ala Thr Gly Thr Cys Cys Cys Thr Cys Gly Cys Ala Gly Thr
 1                   5                  10                  15
Gly Thr Thr Cys Gly Thr Gly Cys Thr Cys Ala Gly Gly Gly Ala Cys
                 20                  25                  30
Ala Ala Cys Thr Gly Thr Gly Gly Ala Thr Thr Gly Thr Ala Gly Thr
                 35                  40                  45
Gly Gly Gly Ala Ala Ala Gly Cys Cys Thr Cys Gly Cys Ala Thr Thr
 50                  55                  60
Cys Thr Gly Thr Gly Cys Cys Thr Gly Cys Ala Gly Gly Ala Ala Thr
 65                  70                  75                  80
Cys Cys Cys Cys Ala Thr Cys Ala Cys Gly Cys Ala Gly
                 85                  90                  95
Thr Cys Thr Cys Thr Gly Thr Ala Thr Thr Thr Gly Cys Thr Cys Gly
                100                 105                 110
Thr Cys Ala Ala Thr Cys Ala Ala Ala Thr Cys Ala Cys Gly Ala Ala
                115                 120                 125
Gly Cys Thr Cys Gly Ala Gly Cys Cys Thr Gly Gly Gly Thr Gly
                130                 135                 140
Thr Thr Thr Gly Ala Cys Cys Ala Thr Cys Thr Gly Thr Gly Ala
145                 150                 155                 160
Ala Thr Cys Thr Gly Cys Ala Gly Ala Ala Gly Cys Thr Cys Thr Ala
                165                 170                 175
Thr Thr Thr Gly Ala Gly Thr Gly Gly Ala Ala Thr Cys Ala Gly
                180                 185                 190
Cys Thr Gly Cys Ala Gly Cys Thr Cys Thr Ala Cys Cys Cys Gly
                195                 200                 205
Thr Thr Gly Gly Gly Gly Thr Gly Thr Thr Gly Ala Cys Ala Ala
                210                 215                 220
Ala Cys Thr Gly Ala Cys Cys Cys Ala Gly Cys Thr Cys Ala Cys Thr
225                 230                 235                 240
```

-continued

```
Thr Ala Thr Cys Thr Gly Gly Gly Thr Cys Thr Gly Gly Ala Cys Gly
                245                 250                 255

Cys Cys Ala Ala Cys Cys Ala Ala Cys Thr Gly Ala Ala Gly Ala Gly
            260                 265                 270

Cys Ala Thr Cys Gly Thr Cys Ala Gly Gly Gly Gly Cys Gly Cys Cys
        275                 280                 285

Thr Thr Thr Gly Ala Cys Ala Ala Cys Cys Thr Cys Ala Ala Gly Ala
    290                 295                 300

Gly Cys Cys Thr Cys Ala Cys Thr Cys Ala Cys Ala Thr Cys Thr Gly
305                 310                 315                 320

Gly Cys Thr Gly Thr Ala Cys Ala Ala Cys Ala Ala Cys Cys Cys Cys
                325                 330                 335

Thr Gly Gly Gly Ala Cys Thr Gly Thr Gly Cys Cys Thr Gly Cys Thr
            340                 345                 350

Cys Ala Gly Ala Cys Ala Thr Cys Cys Thr Gly Thr Ala Cys Cys Thr
        355                 360                 365

Cys Ala Gly Thr Cys Gly Cys Thr Gly Gly Ala Thr Cys Thr Cys Thr
    370                 375                 380

Cys Ala Gly Cys Ala Cys Cys Cys Ala Gly Gly Ala Gly Thr Cys Thr
385                 390                 395                 400

Thr Gly Ala Gly Gly Ala Ala Thr Cys Cys Thr Gly Gly Thr Thr Cys
                405                 410                 415

Cys Thr Ala Cys Ala Ala Thr Gly Thr Cys Ala Ala Cys Cys Cys Cys
            420                 425                 430

Gly Ala Cys Thr Cys Ala Gly Cys Ala Cys Thr Cys Thr Gly Cys Thr
        435                 440                 445

Cys Thr Gly Gly Thr Ala Cys Cys Ala Ala Thr Ala Cys Cys Cys Cys
    450                 455                 460

Cys Gly Thr Cys Cys Gly Thr Gly Cys Gly Gly Thr Cys Ala Cys Cys
465                 470                 475                 480

Gly Ala Gly Gly Cys Cys Ala Gly Cys Ala Cys Thr Ala Gly Cys Cys
                485                 490                 495

Cys Cys Thr Cys Gly Ala Ala Ala Thr Gly Cys Cys Cys Ala Gly Gly
            500                 505                 510

Cys Thr Ala Cys Gly Thr Thr Gly Cys Thr Ala Cys Gly Ala Cys Cys
        515                 520                 525

Ala Cys Gly
    530
```

<210> SEQ ID NO 6
<211> LENGTH: 170
<212> TYPE: PRT
<213> ORGANISM: Artificial Sequence
<220> FEATURE:
<223> OTHER INFORMATION: Synthetic construct

<400> SEQUENCE: 6

```
Ala Cys Pro Ser Gln Cys Ser Cys Ser Gly Thr Thr Val Asp Cys Ser
1               5                   10                  15

Gly Lys Ser Leu Ala Ser Val Pro Ala Gly Ile Pro Ile Thr Thr Gln
            20                  25                  30

Ser Leu Tyr Leu Leu Val Asn Gln Ile Thr Lys Leu Glu Pro Gly Val
        35                  40                  45

Phe Asp His Leu Val Asn Leu Gln Lys Leu Tyr Leu Ser Gly Asn Gln
    50                  55                  60
```

```
Leu Gln Ala Leu Pro Val Gly Val Phe Asp Lys Leu Thr Gln Leu Thr
 65                  70                  75                  80

Tyr Leu Gly Leu Asp Ala Asn Gln Leu Lys Ser Ile Val Arg Gly Ala
                 85                  90                  95

Phe Asp Asn Leu Lys Ser Leu Thr His Ile Trp Leu Tyr Asn Asn Pro
            100                 105                 110

Trp Asp Cys Ala Cys Ser Asp Ile Leu Tyr Leu Ser Arg Trp Ile Ser
            115                 120                 125

Gln His Pro Gly Val Leu Arg Asn Pro Gly Ser Tyr Asn Val Asn Pro
        130                 135                 140

Asp Ser Ala Leu Cys Ser Gly Thr Asn Thr Pro Val Arg Ala Val Thr
145                 150                 155                 160

Glu Ala Ser Thr Ser Pro Ser Lys Cys Pro
                165                 170

<210> SEQ ID NO 7
<211> LENGTH: 669
<212> TYPE: PRT
<213> ORGANISM: Artificial Sequence
<220> FEATURE:
<223> OTHER INFORMATION: Synthetic construct

<400> SEQUENCE: 7

Gly Cys Ala Thr Gly Thr Cys Cys Thr Cys Gly Cys Ala Gly Thr
 1               5                  10                  15

Gly Thr Thr Cys Gly Thr Gly Cys Gly Ala Thr Cys Ala Gly Ala Cys
                 20                  25                  30

Ala Ala Cys Thr Gly Thr Ala Thr Ala Cys Thr Gly Cys Cys Ala Thr
             35                  40                  45

Ala Gly Cys Ala Gly Ala Cys Gly Cys Cys Thr Cys Ala Cys Gly Thr
         50                  55                  60

Cys Thr Gly Thr Gly Cys Cys Thr Gly Cys Ala Gly Gly Ala Ala Thr
 65                 70                  75                  80

Cys Cys Cys Cys Ala Cys Cys Ala Cys Ala Cys Gly Cys Gly Gly Ala
                85                  90                  95

Gly Thr Gly Cys Thr Gly Thr Ala Thr Thr Thr Gly Ala Ala Cys Ala
            100                 105                 110

Gly Cys Ala Ala Thr Cys Ala Gly Ala Thr Cys Ala Cys Gly Ala Ala
         115                 120                 125

Gly Cys Thr Cys Gly Ala Gly Cys Cys Gly Gly Gly Gly Thr Gly Gly
         130                 135                 140

Thr Thr Thr Gly Ala Cys Gly Cys Cys Thr Gly Gly Thr Gly Gly Ala
145                 150                 155                 160

Ala Thr Cys Thr Gly Cys Ala Gly Ala Ala Gly Cys Thr Cys Thr Ala
                165                 170                 175

Thr Thr Thr Gly Ala Gly Thr Gly Gly Gly Ala Ala Thr Cys Ala Gly
            180                 185                 190

Cys Thr Gly Cys Ala Gly Gly Cys Thr Cys Thr Cys Cys Thr Gly
         195                 200                 205

Ala Gly Gly Gly Gly Thr Gly Thr Thr Gly Ala Cys Cys Gly
        210                 215                 220

Cys Cys Thr Gly Gly Thr Gly Ala Ala Thr Cys Thr Gly Cys Ala Gly
225                 230                 235                 240

Ala Ala Gly Cys Thr Gly Thr Gly Gly Thr Thr Gly Ala Ala Cys Ala
                245                 250                 255
```

-continued

```
Gly Cys Ala Ala Cys Cys Ala Gly Cys Thr Gly Ala Cys Cys Thr Cys
            260                 265                 270

Thr Cys Thr Cys Cys Cys Cys Gly Cys Thr Gly Gly Thr Gly Thr Gly
        275                 280                 285

Thr Thr Thr Gly Ala Cys Cys Gly Thr Cys Thr Gly Ala Cys Thr Cys
    290                 295                 300

Ala Ala Cys Thr Gly Ala Cys Ala Cys Gly Ala Cys Thr Gly Gly Ala
305                 310                 315                 320

Thr Cys Thr Thr Gly Gly Thr Gly Gly Cys Ala Ala Cys Cys Ala Gly
                325                 330                 335

Cys Thr Gly Ala Ala Gly Gly Cys Cys Cys Thr Thr Cys Gly Cys Gly
            340                 345                 350

Ala Ala Gly Gly Gly Ala Thr Gly Thr Thr Thr Gly Ala Cys Cys Gly
        355                 360                 365

Cys Thr Thr Gly Gly Thr Thr Ala Ala Thr Cys Thr Gly Cys Ala Gly
    370                 375                 380

Ala Cys Gly Cys Thr Gly Gly Ala Thr Thr Thr Gly Cys Ala Cys Ala
385                 390                 395                 400

Ala Cys Ala Ala Cys Cys Ala Gly Cys Thr Gly Ala Ala Gly Ala Gly
                405                 410                 415

Cys Ala Thr Thr Cys Cys Thr Ala Gly Gly Gly Cys Gly Cys Cys
            420                 425                 430

Thr Thr Thr Gly Ala Cys Ala Ala Cys Cys Thr Cys Ala Ala Gly Ala
        435                 440                 445

Gly Cys Cys Thr Cys Ala Cys Thr Ala Ala Cys Ala Thr Cys Thr Ala
    450                 455                 460

Thr Cys Thr Gly Thr Ala Cys Ala Gly Thr Ala Ala Cys Cys Cys Cys
465                 470                 475                 480

Thr Gly Gly Gly Ala Cys Thr Gly Cys Gly Ala Gly Thr Gly Thr Thr
                485                 490                 495

Cys Gly Gly Ala Cys Ala Thr Cys Cys Thr Cys Thr Ala Thr Cys Thr
            500                 505                 510

Gly Ala Ala Gly Ala Ala Cys Thr Gly Gly Ala Thr Thr Gly Thr Gly
        515                 520                 525

Cys Ala Gly Cys Ala Thr Gly Cys Ala Ala Gly Cys Ala Thr Cys Gly
    530                 535                 540

Thr Gly Ala Ala Thr Cys Thr Ala Cys Gly Gly Gly Gly Cys Cys Ala
545                 550                 555                 560

Thr Gly Gly Gly Gly Gly Ala Gly Thr Thr Gly Ala Thr Ala Ala Cys
                565                 570                 575

Gly Thr Gly Ala Ala Gly Thr Gly Cys Thr Cys Thr Gly Gly Thr Ala
            580                 585                 590

Cys Cys Ala Ala Thr Ala Cys Cys Cys Cys Cys Gly Thr Cys Cys Gly
        595                 600                 605

Thr Gly Cys Gly Gly Thr Cys Ala Cys Cys Gly Ala Gly Gly Cys Cys
    610                 615                 620

Ala Gly Cys Ala Cys Thr Ala Gly Cys Cys Cys Cys Thr Cys Gly Ala
625                 630                 635                 640

Ala Ala Thr Gly Cys Cys Cys Ala Gly Gly Cys Thr Ala Cys Gly Thr
                645                 650                 655

Thr Gly Cys Thr Ala Cys Gly Ala Cys Cys Ala Cys Gly
            660                 665
```

```
<210> SEQ ID NO 8
<211> LENGTH: 216
<212> TYPE: PRT
<213> ORGANISM: Artificial Sequence
<220> FEATURE:
<223> OTHER INFORMATION: Synthetic construct

<400> SEQUENCE: 8

Ala Cys Pro Ser Gln Cys Ser Cys Asp Gln Thr Thr Val Tyr Cys His
1               5                   10                  15

Ser Arg Arg Leu Thr Ser Val Pro Ala Gly Ile Pro Thr Thr Thr Arg
            20                  25                  30

Val Leu Tyr Leu Asn Ser Asn Gln Ile Thr Lys Leu Glu Pro Gly Val
        35                  40                  45

Phe Asp Arg Leu Val Asn Leu Gln Lys Leu Tyr Leu Ser Gly Asn Gln
    50                  55                  60

Leu Gln Ala Leu Pro Glu Gly Val Phe Asp Arg Leu Val Asn Leu Gln
65                  70                  75                  80

Lys Leu Trp Leu Asn Ser Asn Gln Leu Thr Ser Leu Pro Ala Gly Val
                85                  90                  95

Phe Asp Arg Leu Thr Gln Leu Thr Arg Leu Asp Leu Gly Gly Asn Gln
            100                 105                 110

Leu Lys Ala Leu Arg Glu Gly Met Phe Asp Arg Leu Val Asn Leu Gln
        115                 120                 125

Thr Leu Asp Leu His Asn Asn Gln Leu Lys Ser Ile Pro Arg Gly Ala
    130                 135                 140

Phe Asp Asn Leu Lys Ser Leu Thr Asn Ile Tyr Leu Tyr Ser Asn Pro
145                 150                 155                 160

Trp Asp Cys Glu Cys Ser Asp Ile Leu Tyr Leu Lys Asn Trp Ile Val
                165                 170                 175

Gln His Ala Ser Ile Val Asn Leu Arg Gly His Gly Gly Val Asp Asn
            180                 185                 190

Val Lys Cys Ser Gly Thr Asn Thr Pro Val Arg Ala Val Thr Glu Ala
        195                 200                 205

Ser Thr Ser Pro Ser Lys Cys Pro
    210                 215

<210> SEQ ID NO 9
<211> LENGTH: 591
<212> TYPE: PRT
<213> ORGANISM: Artificial Sequence
<220> FEATURE:
<223> OTHER INFORMATION: Synthetic construct

<400> SEQUENCE: 9

Thr Gly Thr Cys Cys Thr Thr Cys Ala Cys Ala Gly Thr Gly Cys Thr
1               5                   10                  15

Cys Cys Thr Gly Cys Ala Gly Cys Gly Gly Ala Ala Cys Cys Gly Ala
            20                  25                  30

Gly Gly Thr Cys Cys Ala Thr Thr Gly Thr Cys Ala Gly Ala Gly Ala
        35                  40                  45

Ala Ala Ala Thr Cys Cys Thr Gly Gly Cys Thr Thr Cys Ala Gly Gly
    50                  55                  60

Thr Cys Cys Cys Thr Gly Cys Cys Gly Gly Ala Ala Thr Cys Cys Cys
65                  70                  75                  80

Ala Ala Cys Cys Ala Cys Ala Cys Ala Ala Gly Gly Gly Thr Gly
                85                  90                  95
```

-continued

```
Cys Thr Gly Thr Ala Cys Cys Thr Gly Cys Ala Cys Gly Thr Cys Ala
                100                 105                 110

Ala Cys Gly Ala Gly Ala Thr Thr Ala Cys Thr Ala Ala Gly Thr Thr
                115                 120                 125

Cys Gly Ala Ala Cys Cys Ala Gly Gly Ala Gly Thr Gly Thr Thr Thr
                130                 135                 140

Gly Ala Cys Cys Gly Cys Cys Thr Gly Gly Thr Cys Ala Ala Cys Cys
145                 150                 155                 160

Thr Gly Cys Ala Gly Cys Ala Gly Cys Thr Gly Thr Ala Thr Cys Thr
                165                 170                 175

Gly Gly Gly Ala Gly Gly Ala Ala Ala Thr Cys Ala Gly Cys Thr Gly
                180                 185                 190

Ala Gly Cys Gly Cys Cys Cys Thr Gly Cys Cys Ala Gly Ala Cys Gly
                195                 200                 205

Gly Cys Gly Thr Gly Thr Thr Cys Gly Ala Thr Cys Gly Ala Cys Thr
                210                 215                 220

Gly Ala Cys Thr Cys Ala Gly Cys Thr Gly Ala Cys Cys Ala Gly Ala
225                 230                 235                 240

Cys Thr Gly Gly Ala Thr Cys Thr Gly Thr Ala Cys Ala Ala Cys Ala
                245                 250                 255

Ala Thr Cys Ala Gly Cys Thr Gly Ala Cys Cys Gly Thr Gly Cys Thr
                260                 265                 270

Gly Cys Cys Thr Cys Cys Gly Gly Gly Thr Cys Thr Thr Thr
                275                 280                 285

Gly Ala Cys Cys Gly Ala Cys Thr Gly Gly Thr Gly Ala Ala Thr Cys
                290                 295                 300

Thr Gly Cys Ala Gly Ala Cys Ala Cys Thr Gly Gly Ala Thr Cys Thr
305                 310                 315                 320

Gly Cys Ala Cys Ala Ala Cys Ala Thr Cys Ala Gly Cys Thr Gly
                325                 330                 335

Ala Ala Gly Thr Cys Thr Ala Thr Cys Cys Cys Ala Gly Ala Gly
                340                 345                 350

Gly Cys Gly Cys Ala Thr Thr Cys Gly Ala Cys Ala Ala Cys Cys Thr
                355                 360                 365

Gly Ala Ala Ala Ala Gly Thr Cys Thr Gly Ala Cys Cys Cys Ala Thr
                370                 375                 380

Ala Thr Thr Thr Gly Gly Cys Thr Gly Thr Thr Thr Gly Gly Gly Ala
385                 390                 395                 400

Ala Thr Cys Cys Thr Thr Gly Gly Gly Ala Cys Thr Gly Cys Gly Cys
                405                 410                 415

Cys Thr Gly Thr Ala Gly Cys Gly Ala Thr Ala Thr Cys Cys Thr Gly
                420                 425                 430

Thr Ala Thr Cys Thr Gly Thr Cys Cys Gly Gly Ala Thr Gly Gly Cys
                435                 440                 445

Thr Gly Gly Gly Ala Cys Ala Gly Cys Ala Thr Gly Cys Ala Gly Gly
                450                 455                 460

Gly Ala Ala Ala Gly Ala Gly Cys Ala Gly Gly Ala Cys Ala Gly
465                 470                 475                 480

Gly Cys Thr Gly Thr Cys Thr Gly Cys Thr Cys Thr Gly Gly Cys Ala
                485                 490                 495

Cys Cys Ala Ala Cys Ala Cys Ala Cys Cys Gly Thr Gly Cys Gly
                500                 505                 510

Gly Gly Cys Thr Gly Thr Cys Ala Cys Cys Gly Ala Gly Gly Cys Ala
```

```
                515                 520                 525
Thr Cys Ala Ala Cys Ala Thr Cys Cys Cys Ala Thr Cys Ala Ala
            530                 535                 540

Ala Gly Thr Gly Thr Cys Cys Thr Gly Gly Cys Thr Ala Cys Gly Thr
545                 550                 555                 560

Gly Gly Cys Ala Ala Cys Ala Ala Cys Cys Ala Gly Ala Thr Cys Thr
                565                 570                 575

Gly Cys Thr Ala Gly Cys Gly Ala Gly Cys Ala Gly Ala Ala Gly
            580                 585                 590

<210> SEQ ID NO 10
<211> LENGTH: 184
<212> TYPE: PRT
<213> ORGANISM: Artificial Sequence
<220> FEATURE:
<223> OTHER INFORMATION: Synthetic construct

<400> SEQUENCE: 10

Cys Pro Ser Gln Cys Ser Cys Ser Gly Thr Glu Val His Cys Gln Arg
1               5                   10                  15

Lys Ser Leu Ala Ser Val Pro Ala Gly Ile Pro Thr Thr Thr Arg Val
            20                  25                  30

Leu Tyr Leu His Val Asn Glu Ile Thr Lys Phe Glu Pro Gly Val Phe
        35                  40                  45

Asp Arg Leu Val Asn Leu Gln Gln Leu Tyr Leu Gly Gly Asn Gln Leu
    50                  55                  60

Ser Ala Leu Pro Asp Gly Val Phe Asp Arg Leu Thr Gln Leu Thr Arg
65                  70                  75                  80

Leu Asp Leu Tyr Asn Asn Gln Leu Thr Val Leu Pro Ala Gly Val Phe
                85                  90                  95

Asp Arg Leu Val Asn Leu Gln Thr Leu Asp Leu His Asn Asn Gln Leu
            100                 105                 110

Lys Ser Ile Pro Arg Gly Ala Phe Asp Asn Leu Lys Ser Leu Thr His
        115                 120                 125

Ile Trp Leu Phe Gly Asn Pro Trp Asp Cys Ala Cys Ser Asp Ile Leu
    130                 135                 140

Tyr Leu Ser Gly Trp Leu Gly Gln His Ala Gly Lys Glu Gln Gly Gln
145                 150                 155                 160

Ala Val Cys Ser Gly Thr Asn Thr Pro Val Arg Ala Val Thr Glu Ala
                165                 170                 175

Ser Thr Ser Pro Ser Lys Cys Pro
            180

<210> SEQ ID NO 11
<211> LENGTH: 220
<212> TYPE: PRT
<213> ORGANISM: Artificial Sequence
<220> FEATURE:
<223> OTHER INFORMATION: Synthetic construct

<400> SEQUENCE: 11

Met Leu Arg Leu Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
        35                  40                  45
```

```
Arg Glu Phe Arg Ala Ser Leu His Lys Gly Leu Asp Ser Ala Val Glu
 50                  55                  60

Val Cys Val Val Tyr Gly Asn Tyr Ser Gln Gln Leu Gln Val Tyr Ser
 65                  70                  75                  80

Lys Thr Gly Phe Asn Cys Asp Gly Lys Leu Gly Asn Glu Ser Val Thr
                 85                  90                  95

Phe Tyr Leu Gln Asn Leu Tyr Val Asn Gln Thr Asp Ile Tyr Phe Cys
                100                 105                 110

Lys Ile Glu Val Met Tyr Pro Pro Pro Tyr Leu Asp Asn Glu Lys Ser
                115                 120                 125

Asn Gly Thr Ile Ile His Val Lys Gly Lys His Leu Cys Pro Ser Pro
            130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
                180                 185                 190

Asn Met Thr Pro Arg Arg Pro Gly Pro Thr Arg Lys His Tyr Gln Pro
                195                 200                 205

Tyr Ala Pro Pro Arg Asp Phe Ala Ala Tyr Arg Ser
                210                 215                 220

<210> SEQ ID NO 12
<211> LENGTH: 116
<212> TYPE: PRT
<213> ORGANISM: Artificial Sequence
<220> FEATURE:
<223> OTHER INFORMATION: Synthetic construct

<400> SEQUENCE: 12

Ile Leu Val Lys Gln Ser Pro Met Leu Val Ala Tyr Asp Asn Ala Val
 1               5                  10                  15

Asn Leu Ser Cys Lys Tyr Ser Tyr Asn Leu Phe Ser Arg Glu Phe Arg
                20                  25                  30

Ala Ser Leu His Lys Gly Leu Asp Ser Ala Val Glu Val Cys Val Val
            35                  40                  45

Tyr Gly Asn Tyr Ser Gln Gln Leu Gln Val Tyr Ser Lys Thr Gly Phe
 50                  55                  60

Asn Cys Asp Gly Lys Leu Gly Asn Glu Ser Val Thr Phe Tyr Leu Gln
 65                  70                  75                  80

Asn Leu Tyr Val Asn Gln Thr Asp Ile Tyr Phe Cys Lys Ile Glu Val
                85                  90                  95

Met Tyr Pro Pro Pro Tyr Leu Asp Asn Glu Lys Ser Asn Gly Thr Ile
                100                 105                 110

Ile His Val Lys
            115

<210> SEQ ID NO 13
<211> LENGTH: 288
<212> TYPE: PRT
<213> ORGANISM: Artificial Sequence
<220> FEATURE:
<223> OTHER INFORMATION: Synthetic construct

<400> SEQUENCE: 13

Met Gly His Thr Arg Arg Gln Gly Thr Ser Pro Ser Lys Cys Pro Tyr
 1               5                  10                  15
```

```
Leu Asn Phe Phe Gln Leu Leu Val Leu Ala Gly Leu Ser His Phe Cys
             20                  25                  30

Ser Gly Val Ile His Val Thr Lys Glu Val Lys Glu Val Ala Thr Leu
         35                  40                  45

Ser Cys Gly His Asn Val Ser Val Glu Glu Leu Ala Gln Thr Arg Ile
 50                  55                  60

Tyr Trp Gln Lys Glu Lys Lys Met Val Leu Thr Met Met Ser Gly Asp
 65                  70                  75                  80

Met Asn Ile Trp Pro Glu Tyr Lys Asn Arg Thr Ile Phe Asp Ile Thr
                 85                  90                  95

Asn Asn Leu Ser Ile Val Ile Leu Ala Leu Arg Pro Ser Asp Glu Gly
            100                 105                 110

Thr Tyr Glu Cys Val Val Leu Lys Tyr Glu Lys Asp Ala Phe Lys Arg
        115                 120                 125

Glu His Leu Ala Glu Val Thr Leu Ser Val Lys Ala Asp Phe Pro Thr
    130                 135                 140

Pro Ser Ile Ser Asp Phe Glu Ile Pro Thr Ser Asn Ile Arg Arg Ile
145                 150                 155                 160

Ile Cys Ser Thr Ser Gly Gly Phe Pro Glu Pro His Leu Ser Trp Leu
                165                 170                 175

Glu Asn Gly Glu Glu Leu Asn Ala Ile Asn Thr Thr Val Ser Gln Asp
            180                 185                 190

Pro Glu Thr Glu Leu Tyr Ala Val Ser Ser Lys Leu Asp Phe Asn Met
        195                 200                 205

Thr Thr Asn His Ser Phe Met Cys Leu Ile Lys Tyr Gly His Leu Arg
    210                 215                 220

Val Asn Gln Thr Phe Asn Trp Asn Thr Thr Lys Gln Glu His Phe Pro
225                 230                 235                 240

Asp Asn Leu Leu Pro Ser Trp Ala Ile Thr Leu Ile Ser Val Asn Gly
                245                 250                 255

Ile Phe Val Ile Cys Cys Leu Thr Tyr Cys Phe Ala Pro Arg Cys Arg
            260                 265                 270

Glu Arg Arg Arg Asn Glu Arg Leu Arg Arg Glu Ser Val Arg Pro Val
        275                 280                 285

<210> SEQ ID NO 14
<211> LENGTH: 330
<212> TYPE: PRT
<213> ORGANISM: Artificial Sequence
<220> FEATURE:
<223> OTHER INFORMATION: Synthetic construct

<400> SEQUENCE: 14

Met Asp Pro Gln Cys Thr Met Gly Leu Ser Asn Ile Leu Phe Val Met
 1               5                  10                  15

Ala Phe Leu Leu Ser Gly Ala Ala Pro Leu Lys Ile Gln Ala Tyr Phe
             20                  25                  30

Asn Glu Thr Ala Asp Leu Pro Cys Gln Phe Ala Asn Ser Gln Asn Gln
         35                  40                  45

Ser Leu Ser Glu Leu Val Val Phe Trp Gln Asp Gln Glu Asn Leu Val
     50                  55                  60

Leu Asn Glu Val Tyr Leu Gly Lys Glu Lys Phe Asp Ser Val His Ser
 65                  70                  75                  80

Lys Tyr Met Gly Arg Thr Ser Phe Asp Ser Asp Ser Trp Thr Leu Arg
                 85                  90                  95
```

```
Leu His Asn Leu Gln Ile Lys Asp Lys Gly Leu Tyr Gln Cys Ile Ile
            100                 105                 110

His His Lys Lys Pro Thr Gly Met Ile Arg Ile His Gln Met Asn Ser
            115                 120                 125

Glu Leu Ser Val Leu Ala Asn Phe Ser Gln Pro Glu Ile Val Pro Ile
            130                 135                 140

Ser Asn Ile Thr Glu Asn Val Tyr Ile Asn Leu Thr Cys Ser Ser Ile
145                 150                 155                 160

His Gly Tyr Pro Glu Pro Lys Lys Met Ser Val Leu Leu Arg Thr Lys
                165                 170                 175

Asn Ser Thr Ile Glu Tyr Asp Gly Ile Met Gln Lys Ser Gln Asp Asn
            180                 185                 190

Val Thr Glu Leu Tyr Asp Val Ser Ile Ser Leu Ser Val Ser Phe Pro
            195                 200                 205

Asp Val Thr Ser Asn Met Thr Ile Phe Cys Ile Leu Glu Thr Asp Lys
            210                 215                 220

Thr Arg Leu Leu Ser Ser Pro Phe Ser Ile Glu Leu Glu Asp Pro Gln
225                 230                 235                 240

Pro Pro Pro Asp His Ile Pro Trp Ile Thr Ala Val Leu Pro Thr Val
                245                 250                 255

Ile Ile Cys Val Met Val Phe Cys Leu Ile Leu Trp Lys Trp Lys Lys
            260                 265                 270

Lys Lys Arg Pro Arg Asn Ser Tyr Lys Cys Gly Thr Asn Thr Met Glu
            275                 280                 285

Arg Glu Glu Ser Glu Gln Thr Lys Lys Arg Glu Lys Ile His Ile Pro
            290                 295                 300

Glu Arg Ser Asp Glu Ala Gln Arg Val Phe Lys Ser Ser Lys Thr Ser
305                 310                 315                 320

Ser Cys Asp Lys Ser Asp Thr Cys Phe Pro
                325                 330

<210> SEQ ID NO 15
<211> LENGTH: 16
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(3)
<223> OTHER INFORMATION: where X is any amino acid
<220> FEATURE:
<221> NAME/KEY: MISC_FEATURE
<222> LOCATION: (5)..(12)
<223> OTHER INFORMATION: where X is any amino acid
<220> FEATURE:
<221> NAME/KEY: MISC_FEATURE
<222> LOCATION: (14)..(15)
<223> OTHER INFORMATION: where X is any amino acid

<400> SEQUENCE: 15

Tyr Xaa Xaa Leu Xaa Xaa Xaa Xaa Xaa Xaa Xaa Tyr Xaa Xaa Leu
1               5                   10                  15

<210> SEQ ID NO 16
<211> LENGTH: 8
<212> TYPE: PRT
<213> ORGANISM: Artificial Sequence
<220> FEATURE:
<223> OTHER INFORMATION: Synthetic construct
<220> FEATURE:
```

```
<221> NAME/KEY: MISC_FEATURE
<222> LOCATION: (1)..(8)
<223> OTHER INFORMATION: where X is any amino acid

<400> SEQUENCE: 16

Xaa Xaa Xaa Xaa Xaa Xaa Xaa Xaa
1               5

<210> SEQ ID NO 17
<211> LENGTH: 151
<212> TYPE: PRT
<213> ORGANISM: Artificial Sequence
<220> FEATURE:
<223> OTHER INFORMATION: Synthetic construct

<400> SEQUENCE: 17

Ala Gln Leu Pro Ile Thr Glu Ala Gln Ser Phe Gly Leu Leu Asp Pro
1               5                   10                  15

Lys Leu Cys Tyr Leu Leu Asp Gly Ile Leu Phe Ile Tyr Gly Val Ile
            20                  25                  30

Leu Thr Ala Leu Phe Leu Arg Val Lys Phe Ser Arg Ser Ala Asp Ala
        35                  40                  45

Pro Ala Tyr Gln Gln Gly Gln Asn Gln Leu Tyr Asn Glu Leu Asn Leu
    50                  55                  60

Gly Arg Arg Glu Glu Tyr Asp Val Leu Asp Lys Arg Gly Arg Asp
65                  70                  75                  80

Pro Glu Met Gly Gly Lys Pro Gln Arg Arg Lys Asn Pro Gln Glu Gly
                85                  90                  95

Leu Tyr Asn Glu Leu Gln Lys Asp Lys Met Ala Glu Ala Tyr Ser Glu
            100                 105                 110

Ile Gly Met Lys Gly Glu Arg Arg Arg Gly Lys Gly His Asp Gly Leu
        115                 120                 125

Tyr Gln Gly Leu Ser Thr Ala Thr Lys Asp Thr Tyr Asp Ala Leu His
    130                 135                 140

Met Gln Ala Leu Pro Pro Arg
145                 150

<210> SEQ ID NO 18
<211> LENGTH: 85
<212> TYPE: PRT
<213> ORGANISM: Artificial Sequence
<220> FEATURE:
<223> OTHER INFORMATION: Synthetic construct

<400> SEQUENCE: 18

Ile Pro Ala Val Val Leu Leu Leu Leu Leu Val Glu Gln Ala Ala
1               5                   10                  15

Ala Leu Gly Glu Pro Gln Leu Cys Tyr Ile Leu Asp Ala Ile Leu Phe
            20                  25                  30

Leu Tyr Gly Ile Val Leu Thr Leu Leu Tyr Cys Arg Leu Lys Ile Gln
        35                  40                  45

Val Arg Lys Ala Ala Ile Thr Ser Tyr Glu Lys Ser Asp Gly Val Tyr
    50                  55                  60

Thr Gly Leu Ser Thr Arg Asn Gln Glu Thr Tyr Glu Thr Leu Lys His
65                  70                  75                  80

Glu Lys Pro Pro Gln
                85

<210> SEQ ID NO 19
```

<211> LENGTH: 153
<212> TYPE: PRT
<213> ORGANISM: Artificial Sequence
<220> FEATURE:
<223> OTHER INFORMATION: Synthetic construct

<400> SEQUENCE: 19

```
Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150
```

<210> SEQ ID NO 20
<211> LENGTH: 235
<212> TYPE: PRT
<213> ORGANISM: Artificial Sequence
<220> FEATURE:
<223> OTHER INFORMATION: Synthetic construct

<400> SEQUENCE: 20

```
Met Ala Leu Pro Val Thr Ala Leu Leu Leu Pro Leu Ala Leu Leu Leu
1               5                   10                  15

His Ala Ala Arg Pro Ser Gln Phe Arg Val Ser Pro Leu Asp Arg Thr
            20                  25                  30

Trp Asn Leu Gly Glu Thr Val Glu Leu Lys Cys Gln Val Leu Leu Ser
        35                  40                  45

Asn Pro Thr Ser Gly Cys Ser Trp Leu Phe Gln Pro Arg Gly Ala Ala
    50                  55                  60

Ala Ser Pro Thr Phe Leu Leu Tyr Leu Ser Gln Asn Lys Pro Lys Ala
65                  70                  75                  80

Ala Glu Gly Leu Asp Thr Gln Arg Phe Ser Gly Lys Arg Leu Gly Asp
                85                  90                  95

Thr Phe Val Leu Thr Leu Ser Asp Phe Arg Arg Glu Asn Glu Gly Tyr
            100                 105                 110

Tyr Phe Cys Ser Ala Leu Ser Asn Ser Ile Met Tyr Phe Ser His Phe
        115                 120                 125

Val Pro Val Phe Leu Pro Ala Lys Pro Thr Thr Thr Pro Ala Pro Arg
    130                 135                 140

Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly
```

```
                    165                 170                 175

Leu Asp Phe Ala Cys Asp Ile Tyr Ile Trp Ala Pro Leu Ala Gly Thr
            180                 185                 190

Cys Gly Val Leu Leu Ser Leu Val Ile Thr Leu Tyr Cys Asn His
        195                 200                 205

Arg Asn Arg Arg Val Cys Lys Cys Pro Arg Pro Val Val Lys Ser
    210                 215                 220

Gly Asp Lys Pro Ser Leu Ser Ala Arg Tyr Val
225                 230                 235

<210> SEQ ID NO 21
<211> LENGTH: 255
<212> TYPE: PRT
<213> ORGANISM: Artificial Sequence
<220> FEATURE:
<223> OTHER INFORMATION: Synthetic construct

<400> SEQUENCE: 21

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
    130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
    210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255

<210> SEQ ID NO 22
<211> LENGTH: 207
<212> TYPE: PRT
<213> ORGANISM: Artificial Sequence
<220> FEATURE:
<223> OTHER INFORMATION: Synthetic construct
```

<400> SEQUENCE: 22

```
Met Asp Lys Asp Cys Glu Met Lys Arg Thr Thr Leu Asp Ser Pro Leu
1               5                   10                  15

Gly Lys Leu Glu Leu Ser Gly Cys Glu Gln Gly Leu His Glu Ile Lys
            20                  25                  30

Leu Leu Gly Lys Gly Thr Ser Ala Ala Asp Ala Val Glu Val Pro Ala
        35                  40                  45

Pro Ala Val Leu Gly Gly Pro Glu Pro Leu Met Gln Cys Thr Ala
50                  55                  60

Trp Leu Asn Ala Tyr Phe His Gln Pro Glu Ala Ile Glu Glu Phe Pro
65                  70                  75                  80

Val Pro Ala Leu His His Pro Val Phe Gln Gln Glu Ser Phe Thr Arg
                85                  90                  95

Gln Val Leu Trp Lys Leu Leu Lys Val Val Lys Phe Gly Glu Val Ile
            100                 105                 110

Ser Tyr Gln Gln Leu Ala Ala Leu Ala Gly Asn Pro Lys Ala Ala Arg
        115                 120                 125

Ala Val Gly Gly Ala Met Arg Gly Asn Pro Val Lys Ile Leu Ile Pro
130                 135                 140

Cys His Arg Val Val Cys Ser Ser Gly Ala Val Gly Asn Tyr Ser Gly
145                 150                 155                 160

Gly Leu Ala Val Lys Glu Trp Leu Leu Ala His Glu Gly His Arg Leu
                165                 170                 175

Gly Lys Pro Gly Leu Gly Gly Ser Ser Gly Leu Ala Gly Ala Trp Leu
            180                 185                 190

Lys Gly Ala Gly Ala Thr Ser Gly Ser Pro Pro Ala Gly Arg Asn
        195                 200                 205
```

<210> SEQ ID NO 23
<211> LENGTH: 186
<212> TYPE: PRT
<213> ORGANISM: Artificial Sequence
<220> FEATURE:
<223> OTHER INFORMATION: Synthetic construct

<400> SEQUENCE: 23

```
Val Gly Ser Leu Asn Cys Ile Val Ala Val Ser Gln Asn Met Gly Ile
1               5                   10                  15

Gly Lys Asn Gly Asp Tyr Pro Trp Pro Pro Leu Arg Asn Glu Phe Arg
            20                  25                  30

Tyr Phe Gln Arg Met Thr Thr Thr Ser Ser Val Glu Gly Lys Gln Asn
        35                  40                  45

Leu Val Ile Met Gly Lys Lys Thr Trp Phe Ser Ile Pro Glu Lys Asn
50                  55                  60

Arg Pro Leu Lys Gly Arg Ile Asn Leu Val Leu Ser Arg Glu Leu Lys
65                  70                  75                  80

Glu Pro Pro Gln Gly Ala His Phe Leu Ser Arg Ser Leu Asp Asp Ala
                85                  90                  95

Leu Lys Leu Thr Glu Gln Pro Glu Leu Ala Asn Lys Val Asp Met Val
            100                 105                 110

Trp Ile Val Gly Gly Ser Ser Val Tyr Lys Glu Ala Met Asn His Pro
        115                 120                 125

Gly His Leu Lys Leu Phe Val Thr Arg Ile Met Gln Asp Phe Glu Ser
        130                 135                 140
```

-continued

```
Asp Thr Phe Phe Pro Glu Ile Asp Leu Glu Lys Tyr Lys Leu Leu Pro
145                 150                 155                 160

Glu Tyr Pro Gly Val Leu Ser Asp Val Gln Glu Glu Lys Gly Ile Lys
                165                 170                 175

Tyr Lys Phe Glu Val Tyr Glu Lys Asn Asp
            180                 185
```

EXPRESSION OF CHIMERIC POLYPEPTIDE WITH VARIABLE LYMPHOCYTE RECEPTORS ON IMMUNE CELLS AND USES FOR TREATING CANCER

CROSS-REFERENCE TO RELATED APPLICATIONS

This application is the National Stage of International Application Number PCT/US2015/014975 filed Feb. 9, 2015, which claims the benefit of priority to U.S. Provisional Application No. 61/938,057 filed Feb. 10, 2014. The entirety of each of these applications is hereby incorporated by reference for all purposes.

INCORPORATION-BY-REFERENCE OF MATERIAL SUBMITTED VIA THE OFFICE ELECTRONIC FILING SYSTEM (EFS-WEB)

The Sequence Listing associated with this application is provided in text format in lieu of a paper copy, and is hereby incorporated by reference into the specification. The name of the text file containing the Sequence Listing is 14078US_revised_ST25.txt. The text file is 34 KB, was created on Dec. 18, 2017, and is being submitted electronically via EFS-Web.

BACKGROUND

Chemotherapy is the standard of care for the treatment of many types of cancer, and alternatives methods for treating cancer are need in situations where chemotherapy is not effective. The human immune system is sometimes able to prevent or slow the growth of cancerous cells through recognition by T cells. In order to improve the ability of immune cells to kill cancerous cells, T cells can be isolated from the blood of a patient and genetically altered to specifically bind proteins expressed on the surface of cancerous cells. When put back into the patient, the modified cells more efficiently target the cancerous cells. CD19 is a protein expressed on cancerous B cells. Brentjens et al. report that T cells altered to bind CD19 can induce remissions of cancer in adults with chemotherapy-refractory acute lymphoblastic leukemia. Sci Transl Med, 2013, 5(177): 177ra38.

Chemotherapy agents typically act by killing cancerous cells but they also affect other circulating cells such as T cells. Dasgupta et al. report engineering immune cells to be resistant to cancer drugs in order to prevent T cell death and enhance tumor cell killing during chemotherapy. Biochem Biophys Res Commun, 2010, 391(1):170-5.

Humans generate T- and B-cell antigen receptors primarily by the assembly of Ig V-(D)-J gene segments and somatic hypermutation. Lampreys and hagfish have an alternative system that is based on variable lymphocyte receptors (VLRs), the diversity of which is generated from leucine-rich repeat (LRR) cassettes. Yu et al., report purification and identification of cell surface antigens using lamprey monoclonal antibodies. Immunol Methods, 2012, 386(0): 43-49. See also Yu et al., A lamprey monoclonal VLR antibody recognizes a novel plasma cell antigen, The J of Immunol, 2013, 190, Abstract 114.11; Han et al. Antigen recognition by variable lymphocyte receptors, Science, 2008 321:1834-183; Hirano et al., The evolution of adaptive immunity in vertebrates, Adv Immunol, 2011, 109:125-57; WO 2013/078425; US 2011/0230374; WO 2010/065407; and WO 2008/016854.

References cited herein are not an admission of prior art.

SUMMARY

This disclosure relates to recombinant cellular expression of chimeric proteins with peptide sequences derived from lymphocyte receptors and uses for treating cancer. In certain embodiments, the disclosure relates to a recombinant vector comprising a nucleic acid that encodes a chimeric protein with a segment with a targeting moiety based on a variable lymphocyte receptor (VLR) capable of binding a tumor associated antigen and a segment with a T cell signal transduction subunit. In certain embodiments, the recombinant vectors are used in immune based cancer treatments.

In certain embodiments, the recombinant vectors comprise a nucleic acid that encodes a chimeric polypeptide comprising a targeting sequence of variable lymphocyte receptor domain or variant thereof, a transmembrane domain, a T cell costimulatory molecule domain, and a signal-transduction component of a T-cell antigen receptor domain such as CD3zeta (CD3Z).

In certain embodiments, the variable lymphocyte receptor domain contains a polypeptide sequence of less than 250 amino acids and 4 or 5 or more segments having the sequence XXLXLXX (SEQ ID NO: 1) wherein X may be any amino acid and L may be, individually and independently at each occurrence, leucine or isoleucine or optionally one L (leucine or isoleucine) may be substituted with any amino acid.

In certain embodiments, the variable lymphocyte receptor has a sequence VXCXXXXL XSVPAXIPTTTXXLXXXX-NXITKXXPGVFDXLXXLXXXXLXXNXLXXX-PXGXFD (SEQ ID NO: 2) wherein X may be any amino acid.

In certain embodiments, the variable lymphocyte receptor has an amino acid sequence disclosed herein such as SEQ ID NO: 4, 6, 8, 10, or variant or a sequence with greater than 80, 85, 90, 95% identity thereto.

In certain embodiments, the nucleic acid sequence has a nucleotide sequence disclosed herein such as SEQ ID NO: 3, 5, 7, or 9 or variant or a sequence with greater than 80, 85, 90, 95% identity thereto.

In certain embodiments, the costimulatory molecule is selected from CD28, CD80, CD86 or fragment or variant.

In certain embodiments, the signal-transduction component of the T-cell antigen receptor comprises an immunoreceptor tyrosine-based activation motif with the consensus sequence YXXLXXXXXXXYXXL (SEQ ID NO: 15) wherein X is any amino acid L is leucine or isoleucine and optionally one or two X are optionally deleted.

In certain embodiments, the recombinant vector further comprises an interleukin sequence such as IL-2 or fragment or variant.

In certain embodiments, the recombinant vector further comprises CD8 or fragment or variant.

In certain embodiments, the recombinant vector further comprises a nucleic acid encoding an enzyme that confers resistance to cellular damage in the presence of a chemotherapy agent.

In certain embodiments, the recombinant vector further comprises a nucleic acid encoding methylguanine methyltransferase (MGMT), dihydrofolate reductase (DHFR), cytidine deaminase (CD), and multidrug resistant protein (MDR-1) or variants thereof.

In certain embodiments, the recombinant vector further comprises a nucleic acid encoding the variable lymphocyte receptor sequence that specifically binds to a tumor associated antigen such as CD5, CD19, CD20, CD30, CD33, CD47, CD52, CD152(CTLA-4), CD274(PD-L1), CD340 (ErbB-2), GD2, TPBG, CA-125, CEA, MAGEA1, MAGEA3, MART1, GP100, MUC1, WT1, TAG-72, HPVE6, HPVE7, BING-4, SAP-1, immature laminin receptor, vascular endothelial growth factor (VEGF-A) or epidermal growth factor receptor (ErbB-1).

In certain embodiments, the disclosure relates to isolated cells comprising the recombinant vectors disclosed herein.

In certain embodiments, the isolated cells are selected from T helper cell, cytotoxic T cell, natural killer T cell, or γδ T cell.

In certain embodiments, the disclosure relates to methods of treating cancer comprising isolating immune cells, e.g. T cells, gamma delta T cells, or NK cells, and mixing with or transferring a recombinant vector disclosed herein into the cells under conditions such that the recombinant vector expresses in the isolated cells a chimeric polypeptide comprising a variable lymphocyte receptor domain or variant, a transmembrane molecule domain, a T cell costimulatory molecule domain, and a signal-transduction component of the T-cell antigen receptor domain providing modified immune cells, T cells, gamma delta T cells, or NK cells; and implanting the modified immune cells, T cells, gamma delta T cells, or NK cells into a subject in need thereof.

In certain embodiments, the recombinant vector encodes an enzyme that confers resistance to cellular damage in the presence of a chemotherapy agent, and an effective amount of the chemotherapy agent is administered to the subject before, during, or after implanting the cells into the a subject.

In certain embodiments, the isolated immune cells, T cells, gamma delta T cells, or NK cells are isolated from the subject to receive the implanted modified cells.

In certain embodiments, the cancer is selected from neuroblastoma, glioblastoma, glioma, breast cancer, prostate cancer, colon cancer, lung cancer, skin cancer, renal cancer, ovarian cancer, pancreatic cancer, stomach cancer, leukemia, lymphoma, or melanoma.

In certain embodiments, the disclosure contemplates recombinant polypeptides, recombinant vectors comprising nucleic acids encoding polypeptides reported herein and expression systems for producing those polypeptides.

BRIEF DESCRIPTION OF THE FIGURES

FIG. 1A illustrates a nucleic acid (SEQ ID NO: 3) that encodes variable lymphocyte receptor that binds to neuroblastoma cells (VLR clone 4).

FIG. 1B shows the amino acid sequence (SEQ ID NO: 4) of the variable lymphocyte receptor translated by the nucleic acid in FIG. 1A.

FIG. 1C illustrates a nucleic acid (SEQ ID NO: 5) that encodes variable lymphocyte receptor that binds to neuroblastoma cells (VLR clone 18).

FIG. 1D shows the amino acid sequence (SEQ ID NO: 6) of the variable lymphocyte receptor translated by the nucleic acid in FIG. 1C.

FIG. 1E illustrates a nucleic acid (SEQ ID NO: 7) that encodes variable lymphocyte receptor that binds to neuroblastoma cells (VLR clone 19).

FIG. 1F shows the amino acid sequence (SEQ ID NO: 8) of the variable lymphocyte receptor translated by the nucleic acid in FIG. 1E.

FIG. 2A shows is a codon optimized VLR sequence (SEQ ID NO: 9) that encodes a protein shown to bind to CD5, the CAR expressing this protein can be used to treat T cell malignancies.

FIG. 2B shows amino acid sequence (SEQ ID NO: 10) of the variable lymphocyte receptor translated by the nucleic acid in FIG. 2A.

FIG. 3 illustrates a method of generating VLR-CAR sequences. Tumor samples or tumor cell lines (e.g., neuroblastoma, B cells, T cells), are isolated from a patient e.g., diagnosed with leukemia, and injected into a lamprey. Tumor specific VLRs are identified and cloned into a chimeric antigen receptor cassette within a lentiviral vector. SP refers to the signal peptide and LTR refers to the long terminal repeat. The vector is transduced into immune cells (T cells, natural killer cells) and re-introduce into the same or a different patient.

FIG. 4A shows data from the screening process using yeast display assays for the isolation of an anti-tumor VLR specifically for neuroblastoma. MACS sorted neuroblastoma are provided in the top right quadrant (FACS sort). Colonies are plated on agar, sequenced and cloned into CAR cassette.

FIG. 4B shows data evidencing T cell activation after transduction using the lentiviral vector containing the cloned cassette of FIG. 4A.

FIG. 5 shows a schematic of the lentiviral vector used to transduce T cells and to measure VLR-CAR expression. Antibodies to the Myc tag are used to show cell surface expression of the VLR-CAR.

FIG. 6A shows a cell count vs Myc tag expression (i.e. cell surface VLR-CAR expression) of naïve Jurkat cells by FACS.

FIG. 6B shows data wherein Jurkat cells were transduced at an MOI 2 with lentiviral vector shown in FIG. 5 and wherein genetically modified cells were identified for chimeric antigen receptor expression using the Myc tag.

FIG. 6C shows data wherein Jurkat cells were transduced at an MOI 10 with lentiviral vector shown in FIG. 5 and wherein genetically modified cells were identified for chimeric antigen receptor expression using the Myc tag.

FIG. 8A shows CD5-VLR-CAR transduced Jurkat cells activated by CD5 expressing cells (as measured by CD69 expression).

FIG. 8B shows cells expressing GFP (control) instead of the CD5-VLR-CAR, similarly transduce as in FIG. 8A, are not activated as monitored by CD69 expression.

FIG. 9A illustrates an embodiment of this disclosure.

FIG. 9B illustrates an embodiment of this disclosure.

DETAILED DESCRIPTION

Figure 7A:
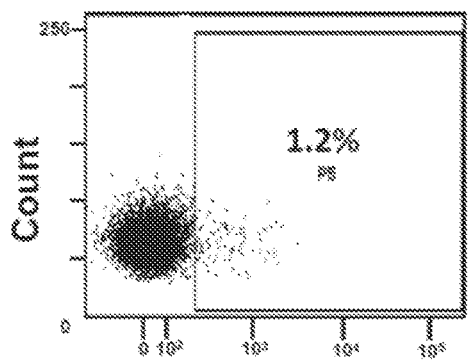
FIG. 7A shows naïve Jurkat cells co-cultured with a BCL cells, and T cell activation is monitored by CD69 expression.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of immunology, medicine, organic chemistry, biochemistry, molecular biology, pharmacology, physiology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

Prior to describing the various embodiments, the following definitions are provided and should be used unless otherwise indicated.

The terms "protein," "peptide," and "polypeptide" refer to compounds comprising amino acids joined via peptide bonds and are used interchangeably. A heterologous polypeptide or polynucleotide refers to a polypeptide or polynucleotide derived from a different source or species. For example, a chimeric polypeptide comprising a targeting sequence refers to a fusion protein in which the targeting sequence is linked to a different polypeptide not associated with the naturally occurring protein from which targeting sequence is derived. A chimeric polypeptide refers to covalent linkage of two distinct polypeptides heterologous to each other. The linkage can be by chemical or recombinant means, for instance. In some cases, the linkage is chemical, wherein a reaction between the antibody moiety and the fusion partner has produced a covalent bond formed between the two molecules to form one molecule. A peptide linker (short peptide sequence) can optionally be included, e.g., between the targeting sequence and the heterologous polypeptide.

The terms "variant" and "mutant" when used in reference to a polypeptide refer to an amino acid sequence that differs by one or more amino acids from another, usually related polypeptide. Variants may be in the form of functioning fragments that may be greater than 25, 50, or 100 amino acids and in some instances less than 100, 150, or 200 amino acids. The variant may have "conservative" changes, wherein a substituted amino acid has similar structural or chemical properties. One type of conservative amino acid substitutions refers to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine More rarely, a variant may have "non-conservative" changes (e.g., replacement of a glycine with a tryptophan). Similar minor variations may also include amino acid deletions or insertions (in other words, additions), or both. Guidance in determining which and how many amino acid residues may be substituted, inserted or deleted without abolishing biological activity may be found using computer programs well known in the art, for example, DNAStar software. Variants can be tested in functional assays. Preferred variants have less than 10%, and preferably less than 5%, and still more preferably less than 2% changes (whether substitutions, deletions, and so on).

The term "nucleic acid" refers to a polymer of nucleotides, or a polynucleotide, as described above. The term is used to designate a single molecule, or a collection of molecules. Nucleic acids may be single stranded or double stranded, and may include coding regions and regions of various control elements, as described below.

The term "a nucleic acid sequence encoding" a specified polypeptide refers to a nucleic acid sequence comprising the coding region of a gene or in other words the nucleic acid sequence which encodes a gene product. The coding region may be present in a cDNA, genomic DNA or RNA form. When present in a DNA form, the oligonucleotide, polynucleotide, or nucleic acid may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present disclosure may contain endogenous enhancers/promoters, splice junctions, intervening sequences, polyadenylation signals, etc. or a combination of both endogenous and exogenous control elements.

The term "recombinant" when made in reference to a nucleic acid molecule refers to a nucleic acid molecule which is comprised of segments of nucleic acid joined together by means of molecular biological techniques. The term "recombinant" when made in reference to a protein or a polypeptide refers to a protein molecule which is expressed using a recombinant nucleic acid molecule. The term recombinant nucleic acid is distinguished from the natural recombinants that result from crossing-over between homologous chromosomes. Recombinant nucleic acids as used herein are an unnatural union of nucleic acids from nonhomologous sources, usually from different organisms.

The terms "vector" or "expression vector" refer to a recombinant nucleic acid containing a desired coding sequence and appropriate nucleic acid sequences necessary for the expression of the operably linked coding sequence in a particular host organism or expression system, e.g., cellular or cell-free. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

Protein "expression systems" refer to in vivo and in vitro (cell free) systems. Systems for recombinant protein expression typically utilize cells transfecting with a DNA expression vector that contains the template. The cells are cultured under conditions such that they translate the desired protein. Expressed proteins are extracted for subsequent purification. In vivo protein expression systems using prokaryotic and eukaryotic cells are well known. Also, some proteins are recovered using denaturants and protein-refolding procedures. In vitro (cell-free) protein expression systems typically use translation-compatible extracts of whole cells or compositions that contain components sufficient for transcription, translation and optionally post-translational modifications such as RNA polymerase, regulatory protein factors, transcription factors, ribosomes, tRNA cofactors, amino acids and nucleotides. In the presence of an expression vectors, these extracts and components can synthesize proteins of interest. Cell-free systems typically do not contain proteases and enable labeling of the protein with modified amino acids. Some cell free systems incorporated encoded components for translation into the expression vector. See, e.g., Shimizu et al., Cell-free translation reconstituted with purified components, 2001, Nat. Biotechnol., 19, 751-755 and Asahara & Chong, Nucleic Acids Research, 2010, 38(13): e141, both hereby incorporated by reference in their entirety.

A "selectable marker" is a nucleic acid introduced into a recombinant vector that encodes a polypeptide that confers a trait suitable for artificial selection or identification (report gene), e.g., beta-lactamase confers antibiotic resistance, which allows an organism expressing beta-lactamase to survive in the presence antibiotic in a growth medium. Another example is thymidine kinase, which makes the host sensitive to ganciclovir selection. It may be a screenable marker that allows one to distinguish between wanted and unwanted cells based on the presence or absence of an expected color. For example, the lac-z-gene produces a beta-galactosidase enzyme which confers a blue color in the presence of X-gal (5-bromo-4-chloro-3-indolyl-β-D-galactoside). If recombinant insertion inactivates the lac-z-gene, then the resulting colonies are colorless. There may be one or more selectable markers, e.g., an enzyme that can complement to the inability of an expression organism to synthesize a particular compound required for its growth (auxotrophic) and one able to convert a compound to another that is toxic for growth. URA3, an orotidine-5' phosphate decarboxylase, is necessary for uracil biosynthesis and can complement ura3 mutants that are auxotrophic for uracil. URA3 also converts 5-fluoroorotic acid into the toxic compound 5-fluorouracil. Additional contemplated selectable markers include any genes that impart antibacterial resistance or express a fluorescent protein. Examples include, but are not limited to, the following genes: $amp^r$, $cam^r$, $tet^r$, $blasticidin^r$, $neo^r$, $hyg^r$, $abx^r$, neomycin phosphotransferase type II gene (nptII), p-glucuronidase (gus), green fluorescent protein (gfp), egfp, yfp, mCherry, p-galactosidase (lacZ), lacZa, lacZAM15, chloramphenicol acetyltransferase (cat), alkaline phosphatase (phoA), bacterial luciferase (luxAB), bialaphos resistance gene (bar), phosphomannose isomerase (pmi), xylose isomerase (xylA), arabitol dehydrogenase (atlD), UDP-glucose:galactose-1-phosphate uridyltransferasel (galT), feedback-insensitive α subunit of anthranilate synthase (OASA1D), 2-deoxyglucose (2-DOGR), benzyladenine-N-3-glucuronide, E. coli threonine deaminase, glutamate 1-semialdehyde aminotransferase (GSA-AT), D-amino acidoxidase (DAAO), salt-tolerance gene (rstB), ferredoxin-like protein (pflp), trehalose-6-P synthase gene (AtTPS1), lysine racemase (lyr), dihydrodipicolinate synthase (dapA), tryptophan synthase beta 1 (AtTSB1), dehalogenase (dhlA), mannose-6-phosphate reductase gene (M6PR), hygromycin phosphotransferase (HPT), and D-serine ammonialyase (dsdA).

In certain embodiments, sequence "identity" refers to the number of exactly matching amino acids (expressed as a percentage) in a sequence alignment between two sequences of the alignment calculated using the number of identical positions divided by the greater of the shortest sequence or the number of equivalent positions excluding overhangs wherein internal gaps are counted as an equivalent position. For example the polypeptides GGGGGG and GGGGT have a sequence identity of 4 out of 5 or 80%. For example, the polypeptides GGGPPP and GGGAPPP have a sequence identity of 6 out of 7 or 85%. In certain embodiments, any recitation of sequence identity expressed herein may be substituted for sequence similarity. Percent "similarity" is used to quantify the similarity between two sequences of the alignment. This method is identical to determining the identity except that certain amino acids do not have to be identical to have a match. Amino acids are classified as matches if they are among a group with similar properties according to the following amino acid groups: Aromatic—F Y W; hydrophobic—A V I L; Charged positive: R K H; Charged negative—D E; Polar-S T N Q.

"Specifically binds" refers to the ability of a specific binding agent (such as an VLR or fragment thereof) of the present disclosure to recognize and bind mature, full-length or partial-length target polypeptide (herein tumor associated antigen), or an ortholog thereof, such that its affinity (as determined by, e.g., Affinity ELISA or assays as described herein) is at least 10 times as great, but optionally 50 times as great, 100, 250 or 500 times as great, or even at least 1000 times as great as the affinity of the same for a random polypeptide of similar overall hydrophobicity.

A "label" refers to a detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes. In one example, a "label receptor" refers to incorporation of a heterologous polypeptide in the receptor. A label includes the incorporation of a radiolabeled amino acid or the covalent attachment of biotinyl moieties to a polypeptide that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionucleotides (such as $^{35}$S or $^{131}$I) fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance.

Variable Lymphocyte Receptor

The jawless vertebrates, lamprey and hagfish, have an adaptive immune system composed of clonally diverse lymphocytes that express variable lymphocyte receptors (VLRs). The germ-line VLRB gene is incomplete, consisting of invariant 5' and 3' constant regions separated by a non-coding intervening sequence. The 5' constant region encodes a signal peptide and part of the N-terminal LRR (LRR-NT). The 3' constant region encodes for a portion of the LRR-CT and an invariant stalk region. The incomplete germ-line gene is flanked by hundreds of partial LRR gene segments. In developing lymphocytes, the flanking LRR gene segments are randomly and sequentially copied into the incomplete VLRB gene. As each LRR gene segment is copied into the locus, it replaces a portion of the intervening sequence. The assembly mechanism continues until all of the intervening sequence is replaced with LRR modules and a functional VLRB is expressed. VLRB gene assembly occurs on only one allele, such that each lymphocyte expresses one VLRB gene.

The mature VLRB gene encodes for a crescent-shaped protein, with amino acid sequence diversity concentrated on the concave surface. The concave surface is composed of parallel β-strands and a C-terminal variable loop. Each LRR subunit contributes one β-strand, and each β-strand has five variable amino acid positions. VLRB antibodies also have variable numbers of LRR subunits. The smallest VLRB antibodies have 4 LRR subunits and the largest have 11 LRR subunits. Each LRR subunit increases the curvature of the concave surface and increases the concave surface area. The C-terminal LRR, LRR-CT, encodes a loop of variable length and sequence composition that projects above the concave surface. Immunization with particulate antigens, such as *Bacillus anthracis* exosporium or human red blood cells (RBCs), induces antigen-binding VLRB+ cells to proliferate and differentiate into plasmacytes. The plasmacytes secrete multivalent VLRB antibodies that circulate in the blood. Each secreted VLRB antibody is composed of identical VLRB polypeptide chains arranged into a pentamer or tetramer of dimers that is held together by disulfide bonds at the C-terminus of the flexible, invariant stalk region. Due to this multivalency, VLRB antibodies bind to their antigens with high avidity.

VLRB cDNAs expressed in mammalian cells lines (HEK-293T and CHO cells) are secreted into the tissue culture supernatant as disulfide-linked, multivalent antibodies, like VLRB in vivo. To isolate antigen-specific VLRB clones, a VLRB cDNA library is prepared from the lymphocytes of immunized lampreys. The VLRB cDNAs are transfected into HEK-293T, and the VLRB-containing tissue culture supernatants are screened for antigen binding.

Yu et al. report the generation of panels of monoclonal VLR antibodies from lamprey larvae immunized with human T cells and the use of a recombinant monoclonal VLR antibody for antigen purification and mass spectrometric identification. See J Immunol Methods, 2012, 386(1-2): 43-9 entitled "Purification and identification of cell surface antigens using lamprey monoclonal antibodies."

In certain embodiments, contemplated recombinant vectors comprise a nucleic acid that encodes a chimeric polypeptide comprising a targeting sequence of variable lymphocyte receptor domain or variant thereof, a transmembrane domain, a T cell costimulatory molecule domain, and a signal-transduction component of a T-cell antigen receptor domain.

Variable lymphocyte receptors typically contain an N-terminal LRR sequence, a C-terminal LRR sequence, and multiple interior LRR modules of approximately 12-25 amino acids. The C-terminal LRR sequence typically contains a variable loop (highly variable insert). Within the interior LRR modules, seven amino acids typically contain one or two leucine or isoleucine, if two, separated by a single amino acid, e.g., (SEQ ID NO: 1) XXLXLXX, that are typically located on the concave surface, wherein X may be any amino acid and L may be leucine or isoleucine. In some instants, one L (leucine or isoleucine) may be substituted with any amino acid.

In certain embodiments, the variable lymphocyte receptor domain contains a polypeptide sequence of less than 250 amino acids and 4 or 5 or more segments having the sequence XXLXLXX (SEQ ID NO: 1) wherein X may be any amino acid and L may be, individually and independently at each occurrence, leucine or isoleucine or one L (leucine or isoleucine) may be substituted with any amino acid.

In certain embodiments, the variable lymphocyte receptor has a sequence VXCXXXXLXS VPAXIPTTTXXLXIT-KXXPGVFDXLXXLXXXXLXXNXLXXXPXGXFD (SEQ ID NO: 2) wherein X may be any amino acid.

In certain embodiments, any of the variable lymphocyte receptors variants disclosed herein are considered to be those that have an altered amino acid sequence, e.g., amino acid substitutions, deletions, insertions, or combinations thereof wherein the altered sequence maintains the ability to specifically bind the antigen of interest. In some embodiment, the substitutions, deletions, insertions are or are not within the 4 or 5 segments having SEQ ID NO: 1 or a segment having SEQ ID NO: 2.

In certain embodiments, the variants contain 1, 2, or 3, amino acid substitutions. In certain embodiments, the variants of SEQ ID NO: 1, 2, 4, 6, 8, or 10, contain 4, 5, 6, 7, 8, 9, or 10 amino acid substitutions. In some embodiment, the substitutions are or are not within the 4 or 5 segments having SEQ ID NO: 1. In certain embodiments, the variant substitutions are conserved substitutions. In certain embodiments, the amino acids are conserved substitutions if they are among a group with similar properties according to the following amino acid groups: Aromatic—F Y W; hydrophobic—A V I L; Charged positive—R K H; Charged negative—D E; Polar—S T N Q.

In certain embodiments, the variants contain 1, 2, or 3, amino acid deletions. In certain embodiments, the variants of SEQ ID NO: 1, 2, 4, 6, 8, or 10, contain 4, 5, 6, 7, 8, 9, or 10 amino acid deletions. In certain embodiments, the deletions are terminal deletions, e.g., starting from the first N-terminal amino acid inward or the last C-terminal amino acid. In certain embodiments, the deletions are interior deletions, e.g., between the first N-terminal amino acid identified in the SEQ ID NO and the last C-terminal amino acid. In certain embodiments, the deletions are not within the 4 or 5 segments having SEQ ID NO: 1.

In certain embodiments, the variants contain 1, 2, or 3, amino acid additions. In certain embodiments, the variants of SEQ ID NO: 1, 2, 4, 6, 8, or 10, contain 4, 5, 6, 7, 8, 9, or 10 amino acid additions. In certain embodiments, the additions are terminal additions, e.g., starting from the first N-terminal amino acid outward or the last C-terminal amino acid. In certain embodiments, the additions are interior deletions, e.g., between the first N-terminal amino acid identified in the SEQ ID NO and the last C-terminal amino acid. In certain embodiments, the deletions are not within the 4 or 5 segments having SEQ ID NO: 1.

A skilled artisan will be able to determine suitable variants of the polypeptide as set forth herein using well-known techniques. In certain embodiments, one skilled in the art may identify suitable areas of the molecule that may be changed without destroying activity by targeting regions not believed to be important for activity. In certain embodiments, one can identify residues and portions of the molecules that are conserved among similar polypeptides. In certain embodiments, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a protein that correspond to amino acid residues which are important for activity or structure in similar proteins. One skilled in the art may opt for chemically similar amino acid substitutions for such predicted important amino acid residues.

One skilled in the art can also analyze the three-dimensional structure and amino acid sequence in relation to that structure in similar polypeptides. In view of such information, one skilled in the art may predict the alignment of amino acid residues of an antibody with respect to its three dimensional structure. In certain embodiments, one skilled in the art may choose not to make radical changes to amino acid residues predicted to be on the surface of the protein, since such residues may be involved in important interactions with other molecules. Moreover, one skilled in the art may generate test variants containing a single amino acid substitution at each desired amino acid residue. The variants can then be screened using activity assays known to those skilled in the art. Such variants could be used to gather information about suitable variants. For example, if one discovered that a change to a particular amino acid residue resulted in destroyed, undesirably reduced, or unsuitable activity, variants with such a change may be avoided. In other words, based on information gathered from such routine experiments, one skilled in the art can readily determine the amino acids where further substitutions should be avoided either alone or in combination with other mutations.

Variants of individual variable lymphocyte receptor may be isolated from combinatorial libraries using protein display technologies, e.g., phage display, yeast surface display, bacterial display, or cell-free systems. See Finlay et al., Methods Mol. Biol., 2011, 681:87-101; Daugherty, Curr. Opin. Struct. Biol., 2007, 17:474-480; Gai & Wittrup, Curr. Opin. Struct. Biol., 2007, 17: 467-473; Zhou et al., MAbs., 2010, 2:508-518; Shen et al., Proc. Nat. Acad. Sci. USA, 2005, 102: 5969-5974. Typically a collection of unique variants are linked through the display platform by expression from corresponding mutated nucleic acids. After exposing/mixing the variants expressed on the display platform with the target molecule, molecule bound variants are identified and/or separated for analysis. Typically, the protein sequence is determined by sequencing an associated nucleic acid in the display platform. For example, in yeast surface display, recombinant yeast cells express variant proteins wherein the yeast cell expresses the variant protein conjugated to a cell wall protein. The yeast cell can contain a plasmid DNA that encodes the variant protein which is expressed on the surface of the yeast cell, and sequencing the plasmid DNA provides the protein sequence of the variant protein. See Gera et al., Protein selection using yeast surface display, Methods, 2013, 60(1):15-26. In phage display, variant proteins are typically conjugated to a bacteriophage coat protein. Cell-based systems also typically rely on the expression of variant proteins conjugated to cell surface proteins, e.g., in bacterial, yeast, and mammalian cells, and the host cell carries a plasmid vector that encodes the variant proteins. Cell-free systems have also been developed wherein the variant protein is conjugated directly to its encoding mRNA, termed ribosome display or mRNA display.

In certain embodiments, the disclosure relates to isolated polypeptides comprising SEQ ID NO: 4, 6, 8, 10, or variants or fusions thereof wherein the amino terminal end or the carbon terminal end of the amino acid sequence are optionally attached to a heterologous amino acid sequence, label, or reporter molecule.

In certain embodiments, the disclosure relates to the recombinant vectors comprising a nucleic acid encoding a polypeptide disclosed herein or chimeric protein thereof.

In certain embodiments, the recombinant vector optionally comprises a mammalian, human, insect, viral, bacterial, bacterial plasmid, yeast associated origin of replication or gene such as a gene or retroviral gene or lentiviral LTR, TAR, RRE, PE, SLIP, CRS, and INS nucleotide segment or gene selected from tat, rev, nef, vif, vpr, vpu, and vpx or structural genes selected from gag, pol, and env.

In certain embodiments, the recombinant vector optionally comprises a gene vector element (nucleic acid) such as a selectable marker region, lac operon, a CMV promoter, a hybrid chicken B-actin/CMV enhancer (CAG) promoter, tac promoter, T7 RNA polymerase promoter, SP6 RNA polymerase promoter, SV40 promoter, internal ribosome entry site (IRES) sequence, cis-acting woodchuck post regulatory regulatory element (WPRE), scaffold-attachment region (SAR), inverted terminal repeats (ITR), FLAG tag coding region, c-myc tag coding region, metal affinity tag coding region, streptavidin binding peptide tag coding region, poly-His tag coding region, HA tag coding region, MBP tag coding region, GST tag coding region, polyadenylation coding region, SV40 polyadenylation signal, SV40 origin of replication, Col E1 origin of replication, fl origin, pBR322 origin, or pUC origin, TEV protease recognition site, loxP site, Cre recombinase coding region, or a multiple cloning site such as having 5, 6, or 7 or more restriction sites within a continuous segment of less than 50 or 60 nucleotides or having 3 or 4 or more restriction sites with a continuous segment of less than 20 or 30 nucleotides.

Immunotherapy and Chimeric Antigen Receptors

In order to improve the ability of immune cells to kill cancerous cells, T cells can be isolated from the blood of a patient and genetically altered to specifically target proteins expressed on the surface of cancerous cells. When put back into the patient, the cells can be more efficient binders of the cancerous cells. CD19 is a protein expressed on cancerous B cells. Brentjens et al. report that T cells altered to bind CD19 can induce remissions of cancer in adults with chemotherapy-refractory acute lymphoblastic leukemia. Sci Transl Med, 2013, 5(177):177ra38.

In certain embodiments, the disclosure relates to recombinants vector comprising a nucleic acid that encodes a chimeric polypeptide comprising a targeting sequence of variable lymphocyte receptor domain or variant thereof, a transmembrane domain, a T cell costimulatory molecule domain, and a signal-transduction component of a T-cell antigen receptor domain.

In certain embodiments, the targeting sequence is a variable lymphocyte receptor domain or any variety of polypeptide sequences capable of selectively binding to a surface protein on target cells, e.g., cancer cells. Other targeting sequences may be variable binding regions of antibodies, single chain antibodies, and antibody mimetic.

In certain embodiments, the costimulatory molecule is selected from CD28 MLRLLLALNLFPSIQVTGNKIL-VKQSPMLVAYDNAVNLSCKYSYNLFSREFRASLHK-GLDS AVEVCVVYGNYSQQLQVYSKTGFNCDGKL-GNESVTFYLQNLYVNQTDIYFCKIEVMYPPP YLDNEKSNGTIIHVKGKHLCPSPLFPGPSKPFWVLV-VVGGVLACYSLLVTVAFIIFWVRSKR SRLLHSDYM-NMTPRRPGPTRKHYQPYAPPRDFAAYRS (SEQ ID NO: 11) or variants or fragment thereof such as the immunoglobulin (Ig) domain of cytotoxic T lymphocyte-associated antigen 4 ILVKQSPMLVAYDNAVNLSCKYSYNLFSRE-FRASLHKGLDSAVEVCVV YGNYSQQLQVYSKTGF-NCDGKLGNESVTFYLQNLYVNQTDIYFCKIEVMYPP-PYLDNEKS NGTIIHVK (SEQ ID NO: 12) or variants or fragment thereof. CD28 is the receptor for CD80 (B7.1) and the disclosure contemplates CD80 as the sequence MGHTRRQGTSPSKCPYLNFFQLL VLAGLSHFCSGVI-HVTKEVKEVATLSCGHNVSVEELAQTRIYWQKEK-KMVLTMMSGDMNI WPEYKNRTIFDITNNLSIVILAL-RPSDEGTYECVVLKYEKDAFKREHLAEVTLSVKAD-FPTPS ISDFEIPTSNIRRIICSTSGGFPEPHLSWLEN-GEELNAINTTVSQDPETELYAVSSKLDFNMTTN HSF-MCLIKYGHLRVNQTFNWNTTKQEHFPDNLLPSWAIT-LISVNGIFVICCLTYCFAPRCRE RRRNERLRRESVRPV (SEQ ID NO: 13) or variants or fragment thereof variants or a sequence with greater than 50, 60, 70, 80, 90, 95% or greater identity thereto. CD28 is also the receptor for CD86 (B7.2) and the disclosure contemplates CD86 as the sequence MDPQCTMGLSNILFV MAFLLS-GAAPLKIQAYFNETADLPCQFANSQNQSLSELVVF-WQDQENLVLNEVYLGKEKF DSVHS-KYMGRTSFDSDSWTLRLHNLQIKDKGLYQCIIHHKK-PTGMIRIHQMNSELSVLANF SQPEIVPISNITENVYIN-LTCSSIHGYPEPKKMSVLLRTKNSTIEYDGIMQKSQD-NVTELYDVS ISLSVSFPDVTSNMTIFCILETDK-TRLLSSPFSIELEDPQPPPDHIPWITAVLPTVIICVMV-FCLIL WKWKKKKRPRNSYKCGTNTMEREESEQTK-KREKIHIPERSDEAQRVFKSSKTSSCDKSDTC FP (SEQ ID NO: 14) or variants or fragment thereof variants or a sequence with greater than 50, 60, 70, 80, 90, 95% or greater identity thereto.

In certain embodiments, the disclosure contemplates using a co-stimulating molecule that is a 20 to 100 or 50 to 150 amino acid fragment of SEQ ID NO: 11-14 or variants thereof or those with 80, 90, 95% or greater identity thereto.

In certain embodiments, the signal-transduction component of the T-cell antigen receptor is a peptide with an immunoreceptor tyrosine-based activation motif with the consensus sequence YXXLXXXXXXXYXXL (SEQ ID NO: 15) wherein X is any amino acid L is leucine or isoleucine, wherein SEQ ID NO: 15 optionally has one or two X amino acid deletions within the middle segment XXXXXXXX (SEQ ID NO: 16). The immunoreceptor tyrosine-based activation motif (underlined) is in the partial CD3-zeta sequence AQLPITEAQSFGLLDPKLCYLL DGILFIYGVILTALFLRVKFSRSADAPAYQQGQNQL YNELNLGRREEYDVLDKRRGRDPE MGGKPQRRKN-PQEGLYNELQKDKMAEAYSEIGMKGERRRGKGH-DGLYQGLSTATKDTY DALHMQALPPR (SEQ ID NO: 17) or fragments or variants, e.g. having 1, 2, or 3 amino acid deletion, addition, or substitution variants, or a sequence with greater than 50, 60, 70, 80, 90, 95% or greater identity thereto.

In certain embodiments, the signal-transduction component of the T-cell antigen receptor is a peptide with a immunoreceptor tyrosine-based activation motif (underlined) with the sequence of immunoglobulin epsilon receptor subunit gamma precursor IPAVVLLLLLLVEQAAAL GEPQLCYILDAILFLYGIVLTLLYCRLKIQVRKAAIT-SYEKSDGVYTGLSTRNQETYETLKH EKPPQ (SEQ ID NO: 18) fragments or variants thereof variants or a sequence with greater than 50, 60, 70, 80, 90, 95% or greater identity thereto.

In certain embodiments, the disclosure relates to recombinant vectors comprising a nucleic acid that encodes a chimeric polypeptide as provided herein further comprising an interleukin sequence such as a human IL-2 signal sequence (amino acids 1-60 of IL-2) MYRMQLLSC IALSLALVTNSAPTSSSTKKTQLQLEHLLLD-LQMILNGINNYKNPKLTRMLTFKFYM PKKATELKHLQCLEEELKPLEEVLNLAQSKNFHLR-PRDLISNINVIVLELKGSE TTFMCEYADETATIVEFL-NRWITFCQSIISTLT (SEQ ID NO: 19), fragments, variants or a sequence with greater than 50, 60, 70, 80, 90, 95% or greater identity thereto.

In certain embodiments, the disclosure relates to recombinant vectors comprising a nucleic acid that encodes a chimeric polypeptide as provided herein further comprising a human CD8 sequence MALPVTALLLPLALLLHAARP-SQFRVSPLDRTWNLGETVELKCQVLLSN PTSGC-SWLFQPRGAAASPTFLLYLSQNKPKAAEGLDTQRF-SGKRLGDTFVLTLSDFRR ENEGYYFCSALSNSIMYFSHFVPVFLPAKPTTTPA-PRPPTPAPTIASQPLSRPEACRP AAGGAVHTRGLD-FACDIYIWAPLAGTCGVLLLSLVITLYCNHRN-RRRVCKCPRPVV KSGDKPSLSARYV (SEQ ID NO: 20) or variant or fragment with a sequence with 50, 60, 70, 80, 90, 95% or greater identity thereto.

In certain embodiments, the disclosure relates to recombinant vectors comprising a nucleic acid that encodes a chimeric polypeptide as provided herein further comprising a human CD137 MGNSCYNIVATLLLVLNFERTRSLQD-PCSNCPAGTFCDNNRNQICSPCPPNSFSSAGGQRTC DICRQCKGVFRTRKECSSTSNAECDCTPGFHCL-GAGCSMCEQDCKQGQELTKKGCKDCCF GTF-NDQKRGICRPWTNCSLDGKSVLVNGTKERDV-VCGPSPADLSPGASSVTPPAPAREPGH SPQIISFFLALTSTALLFLLFFLTLRFSVVKRGRKKLLY-IFKQPFMRPVQTTQEEDGCSCRFPE EEEGGCEL (SEQ ID NO: 21) or variant or fragment with a sequence with 50, 60, 70, 80, 90, 95% or greater identity thereto Immunotherapy In certain embodiments, the disclosure relates to methods of treating cancer comprising isolating T cells, gamma delta T cells, or NK cells and transferring a recombinant vector of disclosed herein into the cells under conditions such that the recombinant vector expresses in the isolated cells a chimeric polypeptide comprising a targeting domain, e.g., variable lymphocyte receptor domain or variant, a transmembrane molecule domain, a T cell co-stimulatory molecule domain, and a signal-transduction component of the T-cell antigen receptor domain providing modified T cells, gamma delta T cells, or NK cells; and implanting the modified T cells, gamma delta T cells, or NK cells into a subject in need thereof.

In certain embodiments, the disclosure relates to recombinants vector comprising a nucleic acid that encodes a chimeric polypeptide comprising a targeting sequence, a transmembrane domain, a T cell co-stimulatory molecule domain, a signal-transduction component of a T-cell antigen receptor domain, and an enzyme that confers resistance to cellular damage in the presence of a chemotherapy agent.

In certain embodiments, the recombinant vector encodes an enzyme that confers resistance to cellular damage in the presence of a chemotherapy agent, and an effective amount of the chemotherapy agent is administered to the subject before, during, or after implanting the cells into the a subject.

Immunocompetent cells exhibit cytotoxicity toward cancer cells and tumorigenic animal models have shown that these cells can infiltrate tumors resulting in tumor regression. Tumor infiltration by immunocompetent cells indicates favorable prognosis in various cancers, such as melanoma, colon, ovarian cancer, basal cell carcinoma, and lung cancer.

Chemotherapy regimens frequently lead to non-specific cellular toxicity to adoptively transferred immunocompetent cells and to hematopoietic stem cells. One strategy to combat drug-induced toxicity is to genetically engineer immune cells to make them drug resistant, e.g., using either drug resistant bone marrow or immunocompetent cells with intrinsic cytotoxic capabilities. Several genes, such as methylguanine methyltransferase (MGMT), dihydrofolate reductase (DHFR), cytidine deaminase (CD), and multidrug resistant protein (MDR-1) can confer drug resistance to anticancer immune cells. Recombinant retroviral vectors, such as lentiviral vectors, are efficient gene transfer systems for the ex vivo modification of cells, e.g., hematopoietic cells. Retroviral gene transfer results in integration of the transferred nucleic acid sequence into the genome of the target cell.

In certain embodiments, the disclosure contemplates recombinant vectors encoding P140KMGMT polypeptide MDKDCEMKRTTLDSPLGKLELSGCEQGLHEIKLLG-KGTSAA DAVEVPAPAAVLGGPEPLMQCTAWLNAYF-HQPEAIEEFPVPALHHPVFQQESFTRQVLWK LLKV-VKFGEVISYQQLAALAGNPKAARAVGGAMRGNP-VKILIPCHRVVCSSGAVGNYSGG LAVKEWLLA-HEGHRLGKPGLGGSSGLAGAWLKGAGATSGSP-PAGRN (SEQ ID NO: 22) and/or L22YDHFR polypeptide VGSLNCIVAVSQNMGIGKNGDYPWPPLRNEFRY-FQRMTTTS SVEGKQNLVIMGKKTWFSIPEKNRPLK-GRINLVLSRELKEPPQGAHFLSRSLDDALKLTEQP ELANKVDMVWIVGGSSVYKEAM-NHPGHLKLFVTRIMQDFESDTFFPEIDLEKYKLL-PEYPG VLSDVQEEKGIKYKFEVYEKND (SEQ ID NO: 23) or a sequence with greater than 80, 90 or 95% identity thereto.

Zielske et al. report lentiviral transduction of P140K MGMT into human CD34(+) hematopoietic progenitors confers significant resistance to BG/BCNU and allows selection in vitro. Mol Ther. 2002, 5(4):381-7. Sawai et al. report protection and in vivo selection of hematopoietic stem cells using temozolomide, O6-benzylguanine, and an alkyltransferase-expressing retroviral vector. Mol Ther. 2001, 3(1):78-87. Maier et al. report F2A sequence linking MGMT (P140K) and MDR1 in a bicistronic lentiviral vector enables efficient chemoprotection of haematopoietic stem cells. Cancer Gene Ther. 2012, 19(11):802-10.

In certain embodiments the immunocompetent cells, e.g., isolated T cells, gamma delta T cells, or NK cells are isolated from the subject to receive the implanted modified cells.

In certain embodiments, the cancer is selected from neuroblastoma, glioblastoma, glioma, breast cancer, prostate cancer, colon cancer, lung cancer, skin cancer, renal cancer, ovarian cancer, pancreatic cancer, stomach cancer, leukemia, lymphoma, or melanoma.

In certain embodiments, the targeting sequence specifically binds to a tumor associated antigen such as CD5, CD19, CD20, CD30, CD33, CD47, CD52, CD152(CTLA-4), CD274(PD-L1), CD340(ErbB-2), GD2, TPBG, CA-125, CEA, MAGEA1, MAGEA3, MART1, GP100, MUC1, WT1, TAG-72, HPVE6, HPVE7, BING-4, SAP-1, immature laminin receptor, vascular endothelial growth factor (VEGF-A) or epidermal growth factor receptor (ErbB-1).

In certain embodiments, the disclosure relates to an isolated cell comprising the recombinant vectors disclosed herein. In certain embodiments, the isolated cells are selected from T helper cells, cytotoxic T cells, natural killer T cells, or gamma delta T cells. These cells may be obtained by isolation from peripheral blood and optionally purified by fluorescent activated cells sorting e.g., mixing cells with fluorescent antibodies or other fluorescent agents and separating the cells by flow cytometry based fluorescent sorting. Another option for cells sorting is to provide magnetic particles that are conjugated to antibodies against a particular antigen on the cell surface. After mixing with a sample, the antibody bound cells are put through a purification column containing a matrix composed of ferromagnetic spheres. When placed on a magnetic separator, the spheres amplify the magnetic field. The unlabeled cells pass through while the magnetically labeled cells are retained within the column. The flow-through can be collected as the unlabeled cell fraction. After a short washing step, the column is removed from the separator, and the magnetically labeled cells are eluted from the column.

CD3 is expressed on all T cells as it is associated with the T cell receptor (TCR). The majority of TCR are made up of alpha beta chains (alpha beta T-cells). Alpha beta T-cells and gamma delta T cells are believed to be derived from a common CD4$^-$CD8$^-$ double-negative precursor thymocytes. Mature gamma delta T cells are CD4$^-$CD8$^-$ double-negative. In contrast, alpha beta T-cells typically become double-positive intermediates (CD4$^+$CD8$^+$) which mature into single-positive (CD4$^+$CD8$^-$) T helper cells or (CD4$^-$CD8$^+$) cytotoxic T cells. Memory cells may be either CD4$^|$ or CD8$^|$. Memory T cells typically express the cell surface protein CD45RO. T cells may be isolated and separated from a human sample (blood or PBMCs) based on the expression of alpha beta T cell receptor (TCR), gamma delta T cell receptor, CD2, CD3, CD4, CD8, CD4 and CD8, NK1.1, CD4 and CD25 and other combinations based on positive or negative selection. TCRγ/δ$^+$ T cells are TCRα/β-, CD2$^+$, CD3$^+$, and CD5$^+$ See also Salot et al., Large scale expansion of Vgamma9Vdelta2 T lymphocytes from human peripheral blood mononuclear cells after a positive selection using MACS "TCR gamma/delta$^+$ T cell isolation kit," J Immunol Methods, 2009, 347(1-2):12-8.

In certain embodiments, the disclosure contemplates methods of engineered immune cells treatments disclosed herein, such as those wherein T cells are engineered to express drug resistant enzymes comparing a VLR with a targeting tumor associated antigen/molecule.

In certain embodiments, the molecule is a tumor associates molecule selected from CD20, CD20, CD30, CD33, CD52, EpCAM, epithelial cell adhesion molecule, gpA33, glycoprotein A33, Mucins, TAG-72, tumour-associated glycoprotein 72, Folate-binding protein, VEGF, vascular endothelial growth factor, integrin αVβ3, integrin α5β1, FAP, fibroblast activation protein, CEA, carcinoembryonic antigen, tenascin, Le$^y$, Lewis Y antigen, CAIX, carbonic anhydrase IX, epidermal growth factor receptor (EGFR; also known as ERBB1), ERBB2 (also known as HER2), ERBB3, MET (also known as HGFR), insulin-like growth factor 1 receptor (IGF1R), ephrin receptor A3 (EPHA3), tumour necrosis factor (TNF)-related apoptosis-inducing ligand receptor 1 (TRAILR1; also known as TNFRSF10A), TRAILR2 (also known as TNFRSF10B) and receptor activator of nuclear factor-κB ligand (RANKL; also known as TNFSF11) and fragments thereof.

In certain embodiments, the subject is at risk of, exhibiting symptoms of, or diagnosed with breast cancer, prostate cancer, colorectal cancer, gastric cancer, lung cancer, skin cancer, bladder cancer, brain cancer, kidney cancer, endometrial cancer, pancreatic cancer, and thyroid cancer.

In certain embodiments, contemplated methods include further administering a second anti-cancer agent such as bevacizumab, gefitinib, erlotinib, temazolamide, docetaxel, cis-platin, 5-fluorouracil, gemcitabine, tegafur, raltitrexed, methotrexate, cytosine arabinoside, hydroxyurea, adriamycin, bleomycin, doxorubicin, daunomycin, epirubicin, idarubicin, mitomycin-C, dactinomycin, mithramycin, vincristine, vinblastine, vindesine, vinorelbine taxol, taxotere, etoposide, teniposide, amsacrine, topotecan, camptothecin, bortezomib, anegrilide, tamoxifen, toremifene, raloxifene, droloxifene, iodoxyfene fulvestrant, bicalutamide, flutamide, nilutamide, cyproterone, goserelin, leuprorelin, buserelin, megestrol, anastrozole, letrozole, vorazole, exemestane, finasteride, marimastat, trastuzumab, cetuximab, dasatinib, imatinib, combretastatin, thalidomide, and/or lenalidomide or combinations thereof.

In certain embodiments, the disclosure contemplates treating or preventing breast cancer using methods of modified immune cells treatments disclosed herein, such as those wherein T cells are engineered to express drug resistant enzymes, in combination with the administration of one or more other anti-cancer agents. In certain embodiments, the disclosure contemplates treating or preventing breast cancer using methods of modified immune cells treatments disclosed herein, such as those wherein T cells are engineered to express drug resistant enzymes, in combination with the administration of trastuzumab and/or lapatinib. In certain embodiments, the disclosure contemplates treating or preventing breast cancer using methods of modified immune cells treatments disclosed herein, such as those wherein T cells are engineered to express drug resistant enzymes, in combination with the administration of docetaxel and cyclophosphamide. In certain embodiments, the disclosure contemplates treating or preventing breast cancer using methods of modified immune cells treatments disclosed herein, such as those wherein T cells are engineered to express drug resistant enzymes, in combination with the administration of docetaxel, carboplatin, and trastuzumab. In certain embodiments, the disclosure contemplates treating or preventing breast cancer using methods of modified immune cells treatments disclosed herein, such as those wherein T cells are engineered to express drug resistant enzymes, in combination with the administration of cyclophosphamide, doxorubicin, and 5-fluorouracil (5-FU). In certain embodiments, the disclosure contemplates treating or preventing breast cancer using methods of modified immune cells treatments disclosed herein, such as those wherein T cells are engineered to express drug resistant enzymes, in combination with the administration of docetaxel, doxorubicin, and cyclophosphamide. In certain embodiments, the disclosure contemplates treating or preventing breast cancer using methods of modified immune cells treatments disclosed herein, such as those wherein T cells are engineered to express drug resistant enzymes, in combination with the administration of doxorubicin and cyclophosphamide followed by paclitaxel or docetaxel. In certain embodiments, the disclosure contemplates treating or preventing breast cancer using methods of modified immune cells treatments disclosed herein, such as those wherein T cells are engineered to express drug resistant enzymes, in combination with the administration of 5-FU, epirubicin, and cyclophosphamide followed by docetaxel or paclitaxel.

In certain embodiments, the disclosure contemplates treating or preventing prostate cancer using methods of modified immune cells treatments disclosed herein, such as those wherein T cells are engineered to express drug resistant enzymes, in combination with the administration of one more other anti-cancer agents. In certain embodiments, the disclosure contemplates treating or preventing prostate cancer using methods of modified immune cells treatments disclosed herein, such as those wherein T cells are engineered to express drug resistant enzymes, in combination with the administration of leuprolide, goserelin, or buserelin. In certain embodiments, the disclosure contemplates treating or preventing prostate cancer using methods of modified immune cells treatments disclosed herein, such as those wherein T cells are engineered to express drug resistant enzymes, in combination with the administration of flutamide, bicalutamide, enzalutamide, or nilutamide. In certain embodiments, the disclosure contemplates treating or preventing prostate cancer using methods of modified immune cells treatments disclosed herein, such as those wherein T cells are engineered to express drug resistant enzymes, in combination with the administration of ketoconazole or aminoglutethimide. In certain embodiments, the disclosure contemplates treating or preventing prostate cancer using methods of modified immune cells treatments disclosed herein, such as those wherein T cells are engineered to express drug resistant enzymes, in combination with the administration of abiraterone, bicalutamide, cabazitaxel, bicalutamide, degarelix, denosumab, docetaxel, enzalutamide, cabazitaxel, leuprolide, prednisone, denosumab, sipuleucel-T, or radium 223 dichloride and combinations thereof.

In certain embodiments, the disclosure contemplates treating or preventing colon cancer using methods of modified immune cells treatments disclosed herein, such as those wherein T cells are engineered to express drug resistant enzymes, in combination with the administration of one more other anti-cancer agents. In certain embodiments, the disclosure contemplates treating or preventing colon cancer using methods of modified immune cells treatments disclosed herein, such as those wherein T cells are engineered to express drug resistant enzymes, in combination with the administration of 5-FU, leucovorin, or capecitabine or combinations thereof. In certain embodiments, the disclosure contemplates treating or preventing colon cancer using methods of modified immune cells treatments disclosed herein, such as those wherein T cells are engineered to express drug resistant enzymes, in combination with the administration of capecitabine and oxaliplatin. In certain embodiments, the disclosure contemplates treating or preventing colon cancer using methods of modified immune cells treatments disclosed herein, such as those wherein T cells are engineered to express drug resistant enzymes, in combination with the administration of 5-FU, leucovorin, and oxaliplatin. In certain embodiments, the disclosure contemplates treating or preventing colon cancer using methods of modified immune cells treatments disclosed herein, such as those wherein T cells are engineered to express drug resistant enzymes, in combination with the administration of leucovorin, 5-FU, and irinotecan. In certain embodiments, the disclosure contemplates treating or preventing colon cancer using methods of modified immune cells treatments disclosed herein, such as those wherein T cells are engineered to express drug resistant enzymes, in combination with the administration of leucovorin, 5-FU, oxaliplatin, and irinotecan.

In certain embodiments, the disclosure contemplates treating or preventing lung cancer using methods of modified immune cells treatments disclosed herein, such as those wherein T cells are engineered to express drug resistant enzymes, in combination with the administration of vinorelbine, etoposide, mitomycin C, gemcitabine, irinotecan, pemetrexed, gefitinib, erlotinib, lapatinib, crizotinib, and a vinca alkaloid or combinations thereof. In certain embodiments, the vinca alkaloid is vinblastine, vincristine, vindesine, or vinorelbine. In certain embodiments, the disclosure contemplates treating or preventing lung cancer using methods of modified immune cells treatments disclosed herein, such as those wherein T cells are engineered to express drug resistant enzymes, in combination with the administration of bevacizumab panitumumab, zalutumumab, nimotuzumab, matuzumab, or cetuximab. In certain embodiments, the disclosure contemplates treating or preventing lung cancer using methods of modified immune cells treatments disclosed herein, such as those wherein T cells are engineered to express drug resistant enzymes, in combination with the administration of a platinum based agent and/or a taxane e.g., paclitaxel and docetaxel or combinations thereof.

In certain embodiments, the disclosure contemplates treating or preventing brain cancer, glioblastoma multiforme, oligodendroglioma, primitive neuroectodermal tumours, ependymomas, or glioma. In certain embodiments, the chimeric protein is optionally administered in combination with temozolomide, procarbazine, carmustine (BCNU), lomustine (CCNU), vincristine, and combinations thereof. In certain embodiments, procarbazine, lomustine (CCNU) and vincristine are combined. In certain embodiments, the chimeric protein is optionally administered in combination with irinotecan, cis-platin, carboplatin, methotrexate, etoposide, bleomycin, vinblastine, actinomycin (Dactinomycin), cyclophosphamide, or ifosfamide.

In certain embodiments, the disclosure contemplates methods combining engineered immune cells treatments disclosed herein, such as those wherein T cells are engineered to express drug resistant enzymes, in combination with temozolomide treatments. Treatment of glioblastoma includes chemotherapy during and after radiotherapy. On average, chemotherapy after surgery and radiotherapy can initially reduce the tumor size.

EXPERIMENTAL

Creation of VLR-CAR Sequences that Bind to Tumor Cells/ Neuroblastoma

Naïve lampreys were serially immunized with intact cells (for example, human T cells, murine B cell leukemia, human neuroblastoma cell line) over 6 weeks. Subsequently, their lymphocytes were harvested and RNA was obtained and converted to cDNA. PCR amplification of the VLR sequences from the cDNA library facilitated cloning of the VLRs into a yeast surface expression library which was used to screen for VLRs that bind to antigens on the target cells by flow cytometry (See FIGS. 3 and 4 illustrate the process used to generate VLR sequences that can be used to target tumor cells.) A similar high throughout process incorporating normal cells or tissue can be used to negatively select VLRs that are likely to generate off-target CAR effects. VLRs meeting the set criteria then are sequenced and cloned into a CAR transgene cassette. The VLR-CAR was subsequently cloned into a lentiviral vector, which was used to produce high titer recombinant lentivirus. The recombinant virus was used to transduce T cells (Jurkat cells). As shown in FIG. 4, anti-neuroblastoma VLR-CAR (generated against the neuroblastoma tumor cell line, SK-N-Be(2)) effectively activated T cells in the presence of stimulatory cells.

VLR Sequences that Bind to B-Cell Leukemia

Figure 7B:
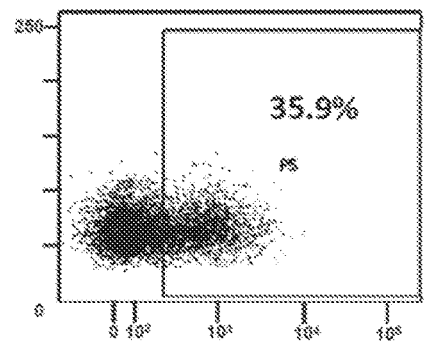
FIG. 7B shows BCL-VLR-CAR transduced Jurkat cells co-cultured with a BCL cells, transduced at MOI 2. Transduced Jurkat cells were incubated with the BCL cell line expressing the target B-cell receptor and monitored by CD69 expression as a measure of T cell activation.
Figure 7C:
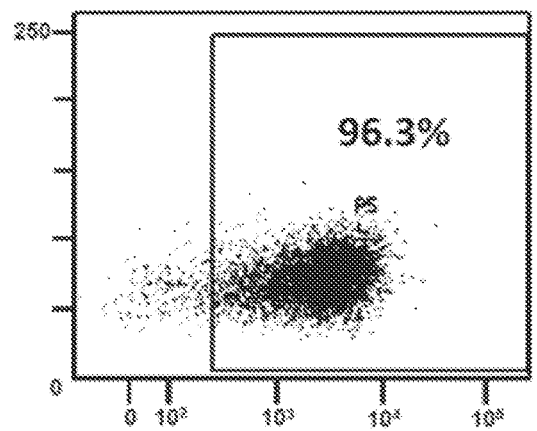
FIG. 7C shows BCL-VLR-CAR transduced Jurkat cells co-cultured with a BCL cells, transduced at MOI 10, and monitored by CD69 expression as a measure of T cell activation.

A CAR was developed that contains a VLR specific for the B-cell receptor of a murine B cell leukemia (BCL) cell line. The CAR design incorporates the anti-BCL-VLR, a Myc tag, CD28 transmembrane domain, and the intracellular CD3ζ signaling domain (FIG. 5). SIN VLR-CAR lentiviral vector was produced at high titer ($\sim 1\times 10^8$) and used to transduce HEK 293T and Jurkat cells. Transduced Jurkat cells demonstrated persistent surface CAR (FIGS. 6A-C) without overt toxicity. To determine whether the VLR was capable of signaling through the CAR, the transduced Jurkat cells were incubated with the BCL cell line expressing the target B-cell receptor. Using this assay, potent T cell activation via the VLR-CAR was demonstrated (FIGS. 7A-C).

VLR Sequences that Bind to T-Cell Leukemia

Yu, C., et al., 2012 identified a VLR sequence that recognizes CD5, which is present, for example, on T cell leukemias. A codon optimized cDNA was synthesized that encodes the VLR, and was cloned into the CAR sequence shown in FIG. 5 in place of the BCL-VLR. High titer virus was generated and used to transduce T cells, similar to the studies described above. Cells transduced with a GFP expressing cassette were not activated in the presence of CD5 expressing cells, but cells transduced with the CD5 VLR-CAR showed increased CD69 expression (FIG. 8A), indicating T cell activation.

What is claimed is:

1. A recombinant vector comprising a nucleic acid that encodes a chimeric polypeptide comprising a targeting sequence of a variable lymphocyte receptor domain, a transmembrane domain, a T cell costimulatory molecule domain, and a signal-transduction component of a T-cell antigen receptor domain, wherein the variable lymphocyte receptor has SEQ ID NO: 4, 6, or 8.

2. The recombinant vector of claim 1, wherein the nucleic acid has SEQ ID NO: 3, 5, or 7 or a sequence with greater than 95% identity thereto.

3. The recombinant vector of claim 1, wherein the costimulatory molecule is selected from CD28, CD80, CD86 or variant or fragment thereto.

4. The recombinant vector of claim 1, wherein the signal-transduction component of the T-cell antigen comprises sequence YXXLXXXXXXXYXXL (SEQ ID NO: 15) wherein X is any amino acid, L is leucine or isoleucine, and one or two X are optionally deleted.

5. The recombinant vector of claim 1, wherein the chimeric polypeptide further comprises an interleukin signal sequence.

6. The recombinant vector of claim 1, wherein the chimeric polypeptide further comprises CD8.

7. The recombinant vector of claim 1, further encoding an enzyme that confers resistance to cellular damage in the presence of a chemotherapy agent.

8. The recombinant vector of claim 1, further encoding methylguanine methyltransferase (MGMT), dihydrofolate reductase (DHFR), cytidine deaminase (CD), and/or multidrug resistant protein (MDR-1) or variant thereof.

9. An isolated cell comprising the recombinant vector of claim 1.

10. The cell of claim 9, selected from T helper cell, cytotoxic T cell, natural killer T cell, or γδ T cell.

11. A recombinant vector comprising a nucleic acid that encodes a chimeric polypeptide comprising a targeting sequence of a variable lymphocyte receptor domain, a transmembrane domain, a T cell costimulatory molecule domain, and a signal-transduction component of a T-cell antigen receptor domain, wherein the variable lymphocyte receptor has SEQ ID NO: 10 encoded by SEQ ID NO: 9.

* * * * *